(12) United States Patent
Moore et al.

(10) Patent No.: US 8,664,225 B2
(45) Date of Patent: Mar. 4, 2014

(54) 1-[2-(2,4-DIMETHYLPHENYLSULFANYL)-PHENYL] PIPERAZINE AS A COMPOUND WITH COMBINED SEROTONIN REUPTAKE, 5-HT3 AND 5-HT1A ACTIVITY FOR THE TREATMENT OF PAIN OR RESIDUAL SYMPTOMS IN DEPRESSION RELATING TO SLEEP AND COGNITION

(75) Inventors: Nicholas Moore, Delmar, NY (US); Tine Bryan Stensbol, Vaerlose (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 819 days.

(21) Appl. No.: 12/527,911

(22) PCT Filed: Mar. 14, 2008

(86) PCT No.: PCT/DK2008/050063
§ 371 (c)(1), (2), (4) Date: Jul. 2, 2010

(87) PCT Pub. No.: WO2008/113359
PCT Pub. Date: Sep. 25, 2008

(65) Prior Publication Data
US 2011/0009422 A1 Jan. 13, 2011

(30) Foreign Application Priority Data

Mar. 20, 2007 (DK) .................................. 2007 00427
Jun. 15, 2007 (WO) ................ PCT/DK2007/050075

(51) Int. Cl.
*A61K 31/4965* (2006.01)

(52) U.S. Cl.
USPC .................................................... 514/255.03

(58) Field of Classification Search
None
See application file for complete search history.

(56) References Cited

U.S. PATENT DOCUMENTS

| 7,144,884 B2 | 12/2006 | Ruhland et al. | |
|---|---|---|---|
| 2004/0014771 A1* | 1/2004 | Bartoszyk et al. | 514/254.09 |
| 2005/0014740 A1 | 1/2005 | Ruhland et al. | |
| 2006/0084662 A1 | 4/2006 | Ruhland et al. | |

FOREIGN PATENT DOCUMENTS

| WO | 03029232 A1 | 4/2003 |
|---|---|---|
| WO | 2007144005 A1 | 12/2007 |

OTHER PUBLICATIONS

Duman et al. (J Pharmacol Sci 94, 161-165 (2004).*
Jung et al. (J. Gen. Intern. Med., 1997, vol. 12, pp. 384-389).*
Melzack et al., "Central Neuroplasticity and Pathological Pain", Acad. Sci., 933, 157-174 (2001).
Namaka et al., "A Treatment Algorithm for Neuropathic Pain", Clinical Therapeutics, vol. 26, No. 7 (2004).
Briley "Clinical experience with dual action antidepressants in different chronic pain syndromes", Hum Psychopharmacol Clin Exp (2004); 19: S21-S25.
Sindrup et al., "Antidepressants in the Treatment of Neuropathic Pain", Basic & Clinical Pharmacology & Toxicology, (2005), 96, 399-409.
Fisbain et al., "Evidence-Based Data from Animal and Human Experimental Studies on Pain Relief with Antidepressants: A Structured Review", Pain Med. 4, 310-316, (2000).
Fava "Pharmacological approaches to the treatment of residual symptoms", Journal of Psychopharmacology 20(3) (2006) 29-34.
Lam, "Sleep disturbances and depression: a challenge for antidepressants", International Clinical Psychopharmacology (2006), vol. 21 (suppl 1), S25-S29.
Mayers et al., "Antidepressants and their effect on sleep", Hum Psychopharmacol Clin Exp (2005); 20: 533-559.
DeBattista et al., "A Placebo-Controlled, Randomized, Double-Blind Study of Adjunctive Bupropion Sustained Release in the Treatment of SSRI-Induced Sexual Dysfunction", J. Clin. Psych., 66:7, 844-848 (2005).
Fanselow, "Conditional and Unconditional Components of Post-Shock Freezing", The Pavlovian Journal of Biological Science, 15, 177-182 (1980).
Anagnostaras et al., "Hippocampus and Contextual Fear Conditioning: Recent Controversies and Advances", Hippocampus, 11, 8-17 (2001).
Anagnostaras et al., "Temporally Graded Retrograde Amnesia of Contextual Fear after Hippocampal Damage in Rats: Within-Subjects Examination", The Journal of Neuroscience, (1999), 19(3): 1106-1114.
Phillips et al., "Differential Contribution of Amygdala and Hippocampus to Cued and Contextual Fear Conditioning", Behavioral Neuroscience, (1992), vol. 106, No. 2, 274-285.

(Continued)

*Primary Examiner* — James D Anderson
*Assistant Examiner* — William Lee
(74) *Attorney, Agent, or Firm* — Fish & Richardson P.C.

(57) ABSTRACT

The use of 1-[2-(2,4-dimethylphenylsulfanyl)phenyl]piperazine in the treatment of pain and residual symptoms in depression is provided.

(I)

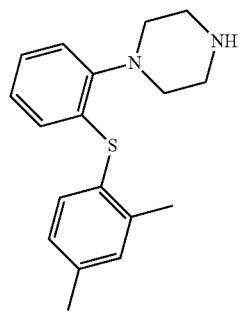

5 Claims, 26 Drawing Sheets

(56) References Cited

OTHER PUBLICATIONS

Figure 1:
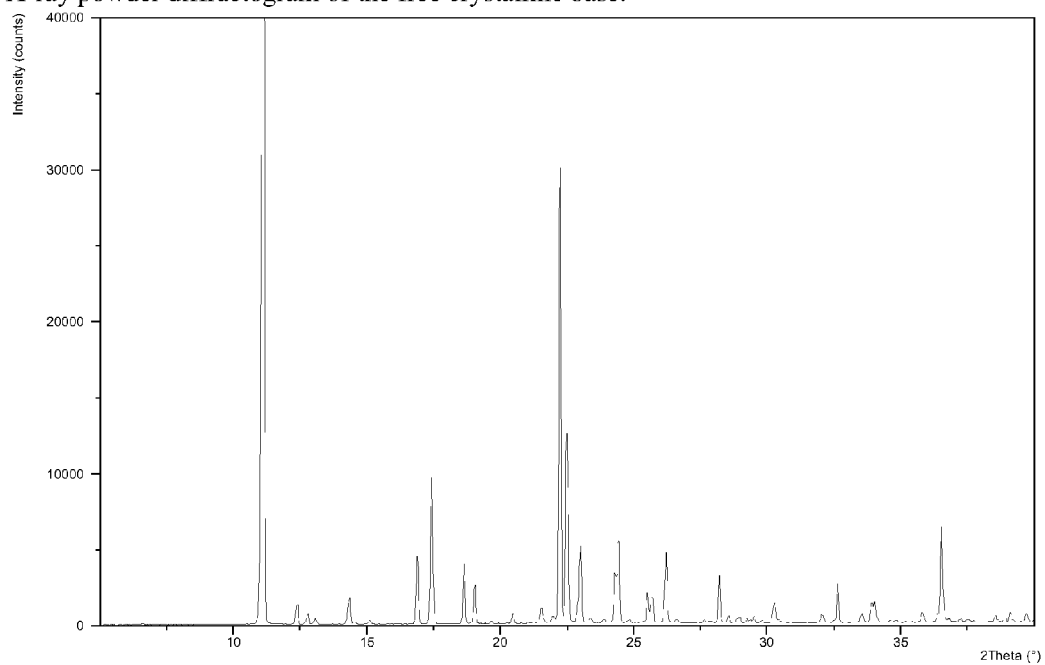

Bennett et al., "A peripheral mononeuropathy in rat that produces disorders of pain sensation like those seen in man", Pain, 33, (1988) 87-107.

Atkinson et al., "Effects of noradrenergic and serotonergic antidepressants on chronic low back pain intensity"; Pain; vol. 83; pp. 137-145 (1999).

Bendtsen et al., "A non-selective (amitriptyline), but not a selective (citalopram), serotonin reuptake inhibitor is effective in the prophylactic treatment of chronic tension-type headache"; Journal of Neurology, Neurosurgery, and Psychiatry; vol. 61; pp. 285-290 (1996).

Dworkin et al., "Pharmacologic management of neuropathic pain: Evidence-based recommendations"; Pain; vol. 132; pp. 237-251 (2007).

Max et al., "Effects of Desipramine, Amitriptyline, and Fluoxetine on Pain in Diabetic Neuropathy"; The New England Journal of Medicine; vol. 326, No. 19; pp. 1250-1256 (1992).

Norregaard et al., "A randomized controlled trial of citalopram in the treatment of fibromyalgia"; Pain; vol. 61; pp. 445-449 (1995).

Schreiber et al., "From selective to highly selective SSRIs: A comparison of the antinociceptive properties of fluoxetine, fluvoxamine, citalopram and escitalopram"; European Neuropsychopharmacology; vol. 16, pp. 464-468 (2006).

Morimoto, Application of antidepressants in chronic pain, Focused on SSRIs and SNRIs, Antidepressants as adjuvant analgesics in chronic pain—Clinical pharmacology and efficacy, Igaku no Ayumi (Advances in Medicine), vol. 211, No. 5, pp. 535-538, 2004 (With English Translation).

\* cited by examiner

X-ray powder diffractogram of the hydrobromide hemihydrate

X-ray powder diffractogram of the hydrochloride salt:

X-ray powder diffractogram of the hydrochloride monohydrate:

X-ray powder diffractogram of the fumarate:

X-ray powder diffractogram of the maleate:

X-ray powder diffractogram of the phosphate:

X-ray powder diffractogram of the nitrate salt

1-[2-(2,4-DIMETHYLPHENYLSULFANYL)-PHENYL] PIPERAZINE AS A COMPOUND WITH COMBINED SEROTONIN REUPTAKE, 5-HT3 AND 5-HT1A ACTIVITY FOR THE TREATMENT OF PAIN OR RESIDUAL SYMPTOMS IN DEPRESSION RELATING TO SLEEP AND COGNITION

CROSS REFERENCE TO PRIOR APPLICATIONS

This is a U.S. National Phase application under 35 U.S.C. §371 of International Patent Application No. PCT/DK2008/050063, filed Mar. 14, 2008, and claims the benefit of Danish Application No. PA 200700427, filed Mar. 20, 2007 and International Application No. PCT/DK2007/050075, filed Jun. 15, 2007 both of which are incorporated by reference herein. The International Application published in English on Sep. 25, 2008 as WO 2008/113359 under PCT Article 21(2).

BACKGROUND

The compound 1-[2-(2,4-dimethylphenylsulfanyl)phenyl]piperazine is disclosed in the international patent application WO 03/029232. The compound is said to be an inhibitor of the serotonin transporter and to have affinity for the serotonin receptor 2C (5-HT$_{2C}$), and as such be useful in the treatment of mood disorders, such as depression and anxiety.

As shown in the examples, however, the compound has a broader pharmacological profile which makes the compound useful in the treatment of other diseases as well. This pharmacological profile has also been disclosed in the international patent application WO 2007/144005 together with the use of said compound for the treatment of additional diseases.

The perception of pain is more complicated than a direct transmission of signals from an injured part of the body to specific receptors in the brain, and wherein the pain perceived is proportional to the injury. Rather, damage to peripheral tissue and injury to nerves may cause alterations in the central neural structures involved in pain perception affecting subsequent pain sensitivity. This neuroplasticity may bring about a central sensitization in response to longer lasting noxious stimuli, which may manifest itself as e.g. chronic pain, i.e. that the perception of pain remains even after the noxious stimulus has stopped, or as hyperalgesia, i.e. an increased response to a stimulus, which is normally painful. On of the more mysterious and dramatic examples of this is the "phantom limb syndrome", i.e. the persistence of pain that existed in a limb prior to its amputation. For a recent review of central neuroplasticity and pain see Melzack et al in *Ann. N.Y. Acad. Sci.*, 933, 157-174, 2001.

Chronic pain, such as neuropathic pain manifests itself differently than other types of pain, e.g. somatic or visceral pain. The pain is often described as shooting, burning, pins and needles, numb or stabbing. Common causes of neuropathic pain include alcoholism, amputation, back, leg and hip problems, chemotherapy, diabetes, HIV, multiple sclerosis, spine surgery, and herpes zoster virus infection.

The central component to chronic pain may explain why chronic pain, such as e.g. neuropathic pain often responds poorly to classical analgesics, such as non-steroid anti-inflammatory drugs (NSAIDS) and opioid analgesics. Tricyclic antidepressants (TCA), typified by amitryline, have become standard for the treatment of neuropatic pain, and the effect is believed to be mediated by the combined inhibitory effect on the serotonin transporter and the norepinephrine transporter [*Clin Ther.*, 26, 951-979, 2004]. More recently, the so-called dual action antidepressants having an inhibitory effect on both the serotonin and the norepinephrine reuptake have been used clinically for the treatment of neuropatic pain [*Human Psychopharm.*, 19, S21-S25, 2004]. Examples of dual acting antidepressants are venlafaxine and duloxetine, and this class of antidepressants is often referred to as SNRI.

Data on the use of selective serotonine reuptake inhibitors (SSRI) for neuropathic pain is scarce, but generally suggest a limited effect [*Bas. Clin. Pharmacol.*, 96, 399-409, 2005]. In fact, it has been hypothesised that SSRI's are only weakly antinociceptive in and of themselves but that inhibition of the serotonin transporter augments the antinociceptive effect of norepinephrine reuptake inhibition. This notion is supported by a review of 22 animal and five human studies showing that SNRI's have superior antinociceptive effect compared to norepinephrine reuptake inhibitors, which again are superior to SSRI [*Pain Med.* 4, 310-316, 2000].

The use of tricyclic antidepressants is, however, associated with known, anticholinergic side effects, such as e.g. drowsiness, anxiety, restlessness, and cognitive and memory difficulties. Hence, there is a need in the art to find alternative ways of treating pain.

Depressed patients receiving antidepressants, such as e.g. SSRI's often respond only partially to the treatment in the sense that symptoms, in particular relating to sleep and cognition, remain [*J. Psychopharmacol.*, 20(3), 29-34, 2006]. These residual symptoms increase the risk of relapse and is of general disturbance to the patient.

SUMMARY OF THE INVENTION

In one embodiment, the invention relates to a method of treating pain or residual symptoms in depression, the method comprising the administration of a therapeutically effective amount of 1-[2-(2,4-dimethylphenylsulfanyl)-phenyl]piperazine and a pharmaceutically acceptable acid addition salt thereof (compound I) to a patient in need thereof.

In one embodiment, the invention relates to the use of 1-[2-(2,4-dimethylphenylsulfanyl)phenyl]piperazine and a pharmaceutically acceptable acid addition salt thereof in the manufacture of a medicament for the treatment of pain or residual symptoms in depression.

In one embodiment, the invention relates to 1-[2-(2,4-dimethylphenyl-sulfanyl)phenyl]piperazine and pharmaceutically acceptable acid addition salts thereof for use in the treatment of pain or residual symptoms in depression.

FIGURES

FIG. 1: XRPD of crystalline base of compound I

Figure 2:
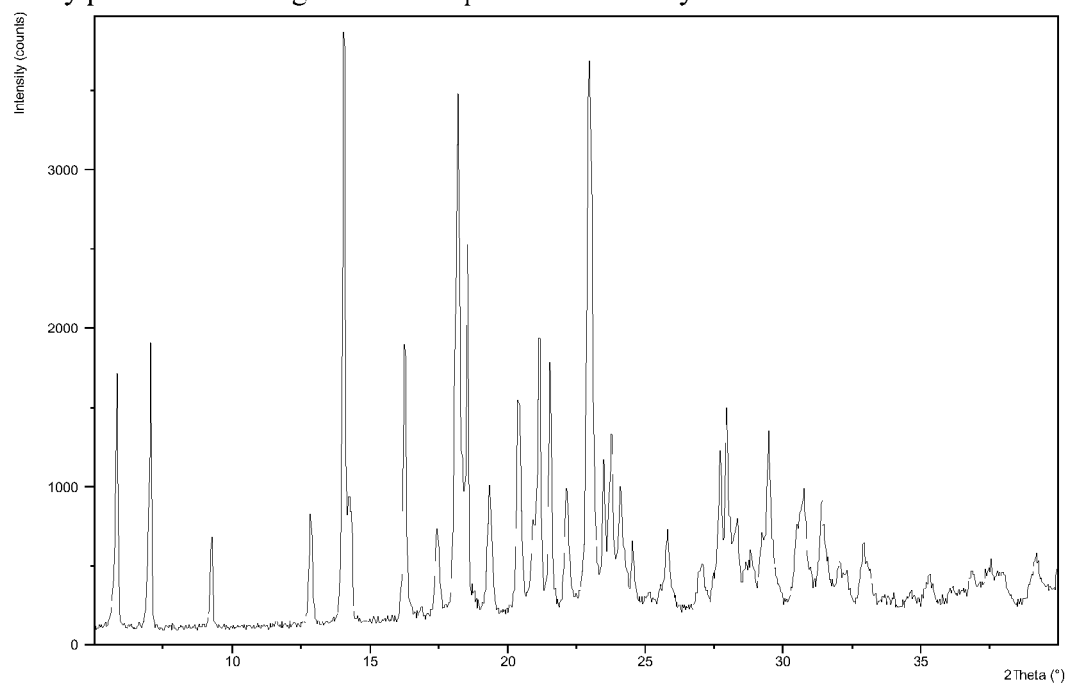

FIG. 2: XRPD of alpha form of hydrobromide salt of compound I

Figure 3:
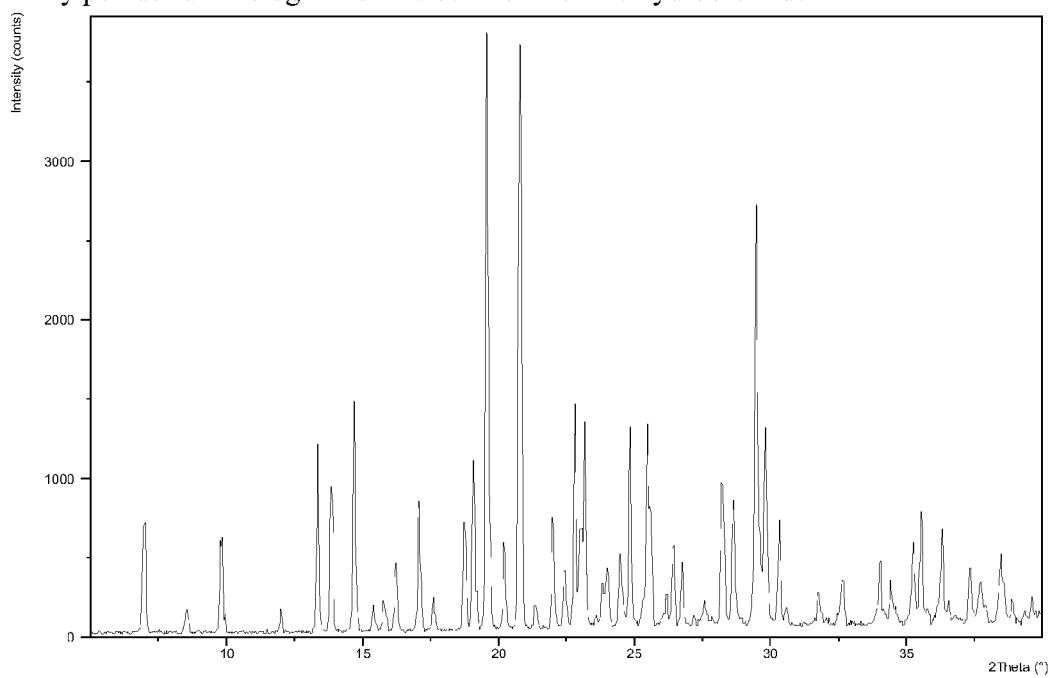

FIG. 3: XRPD of beta form of hydrobromide salt of compound I

Figure 4:
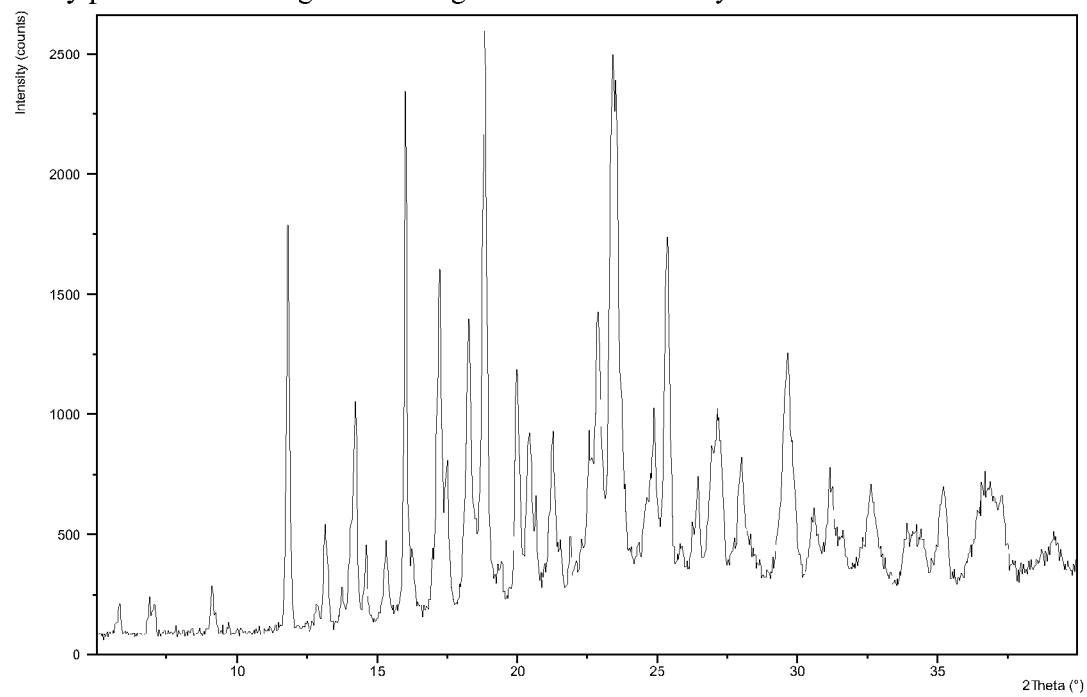

FIG. 4: XRPD of gamma form of hydrobromide salt of compound I

Figure 5:
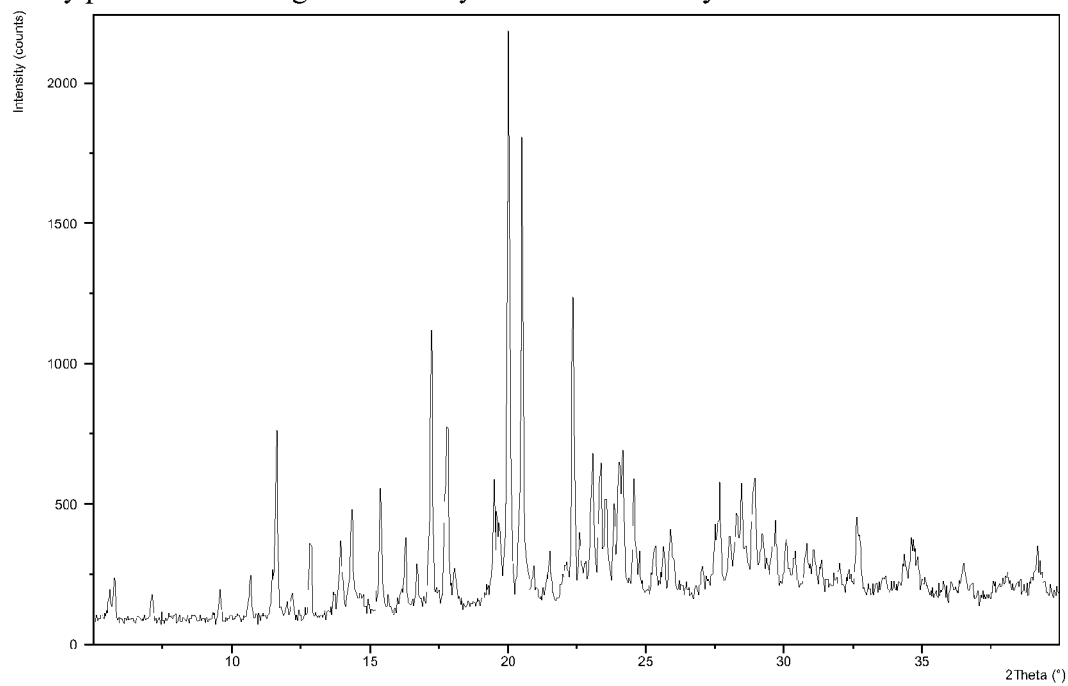

FIG. 5: XRPD of hemi hydrate of hydrobromide salt of compound I

Figure 6:
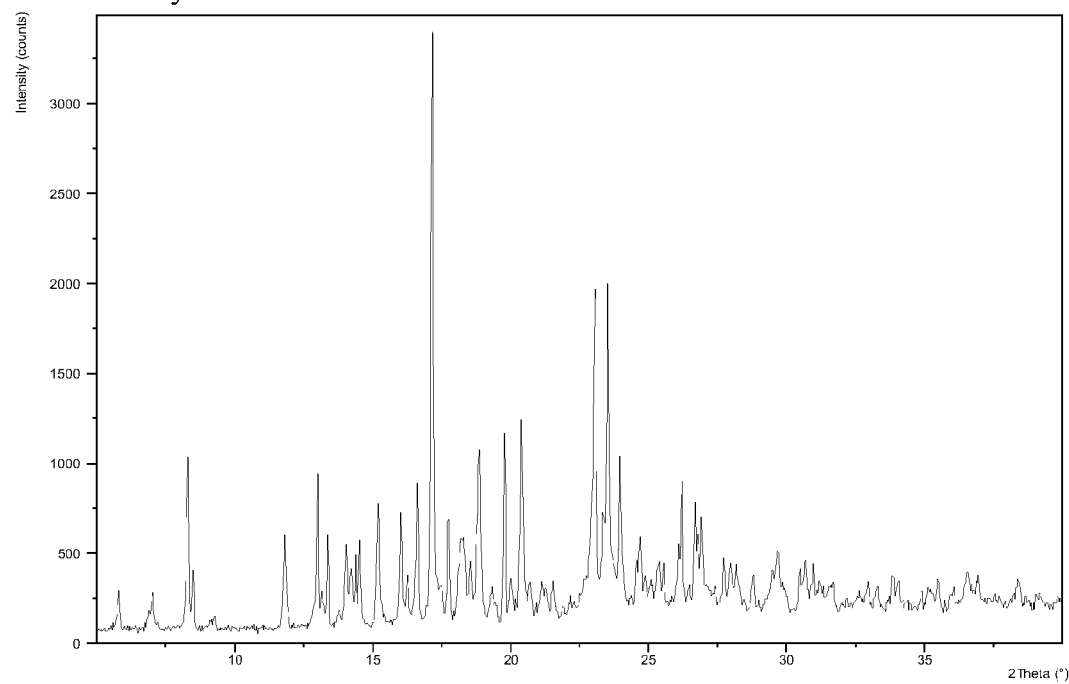

FIG. 6: XRPD of the mixture of the ethyl acetate solvate and the alpha form of the hydrobromide salt of compound I FIG. 7: XRPD of hydrochloride salt of compound I FIG. 8: XRPD of monohydrate of hydrochloride salt of compound I FIG. 9: XRPD of mesylate salt of compound I FIG. 10: XRPD of fumarate salt of compound I FIG. 11: XRPD of maleate salt of compound I FIG. 12: XRPD of meso-tatrate salt of compound I FIG. 13: XRPD of L-(+)-tatrate salt of compound I FIG. 14: XRPD of D-(−)-tatrate salt of compound I FIG. 15: XRPD of sulphate salt of compound I FIG. 16: XRPD of phosphate salt of compound I FIG. 17: XRPD of nitrate salt of compound I FIG. 18: Effect of compound I in the intradermal formalin test. X-axis shows the amount of compound administered; Y-axis shows the amount of time (sec) spent licking the paw. FIG. 18a: Response in the 0-5 minutes period; FIG. 18b: Response in the 20-30 minutes period FIG. 19a: Extra-cellular acetylcholine levels in prefrontal cortex in freely moving rats upon administration of 1-[2-(2,4-dimethylphenylsulfanyl)phenyl]piperazine HBr salt.

Figure 19A:
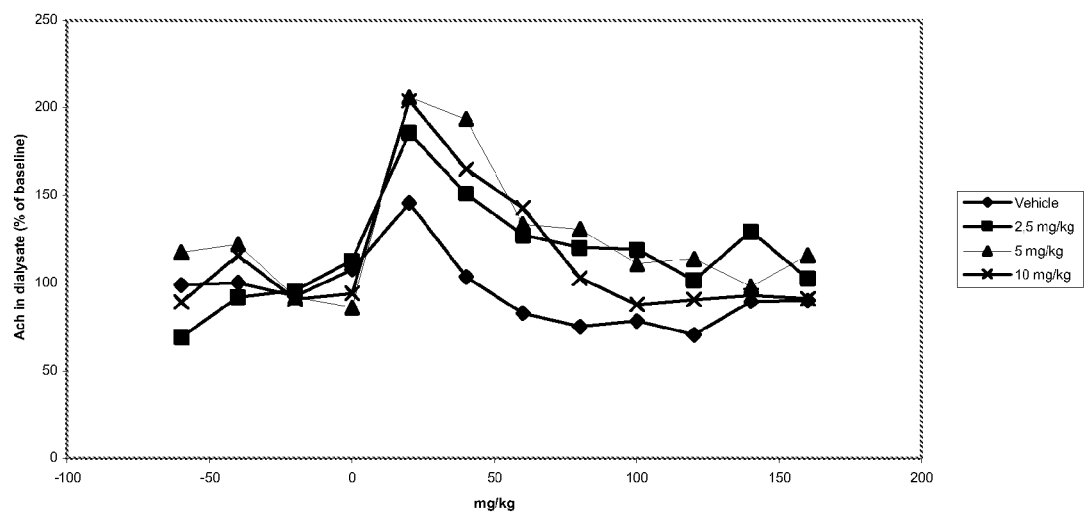
Figure 19B:
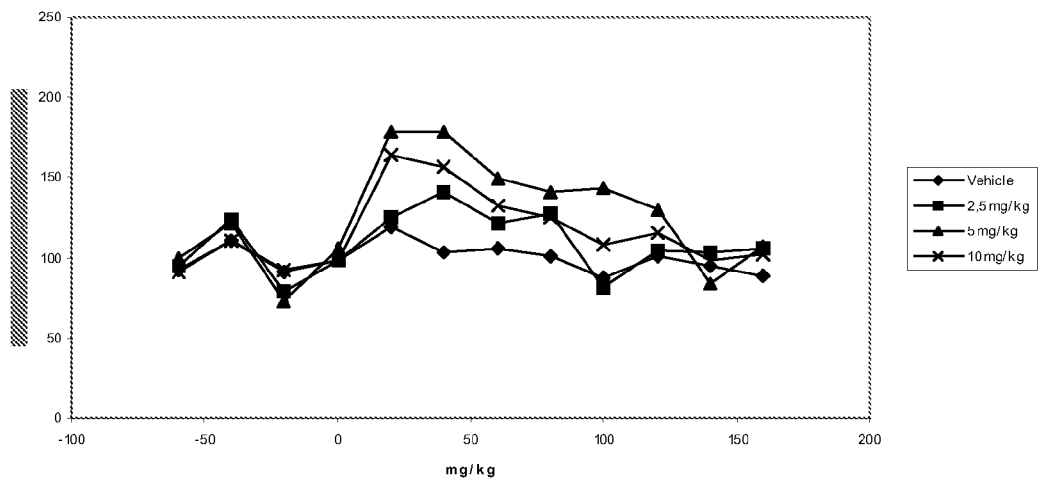

FIG. 19b: Extra-cellular acetylcholine levels in ventral hippocampus in freely moving rats upon administration of 1-[2-(2,4-dimethylphenylsulfanyl)phenyl]-piperazine HBr salt.

Figure 20:
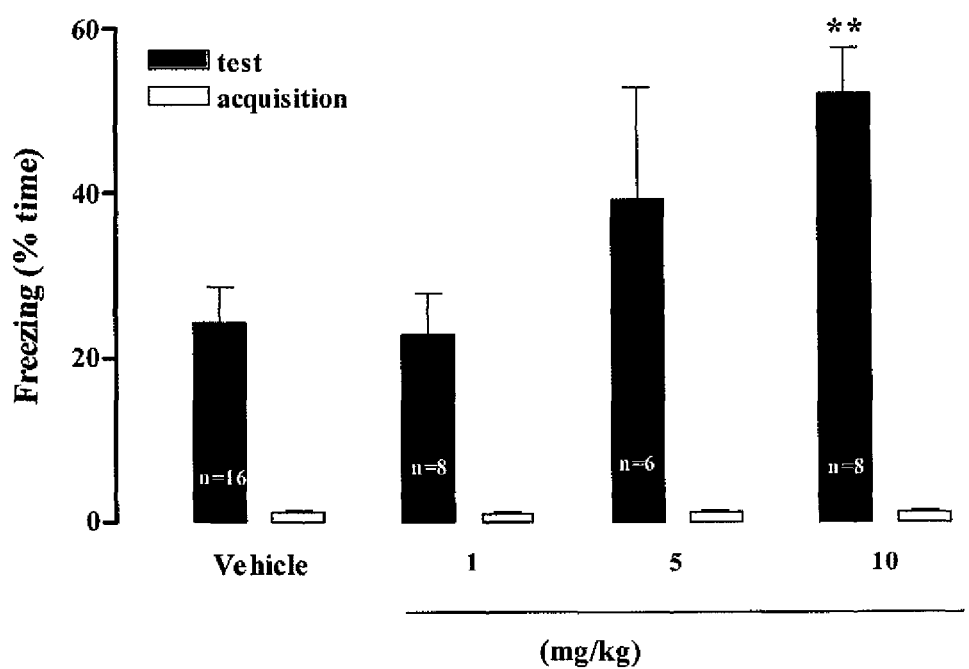

FIG. 20: Effect of 1-[2-(2,4-dimethylphenylsulfanyl)phenyl]piperazine HBr salt on contextual fear conditioning in Sprague-Dawley rats when given 60 minutes before acquisition. Freezing behaviour was scored during 58-s habituation period prior to the foot shock US (pre-shock acquisition) (white bars). Freezing behaviour was measured 24 h after the training (retention test) (black bars).

Figure 21:
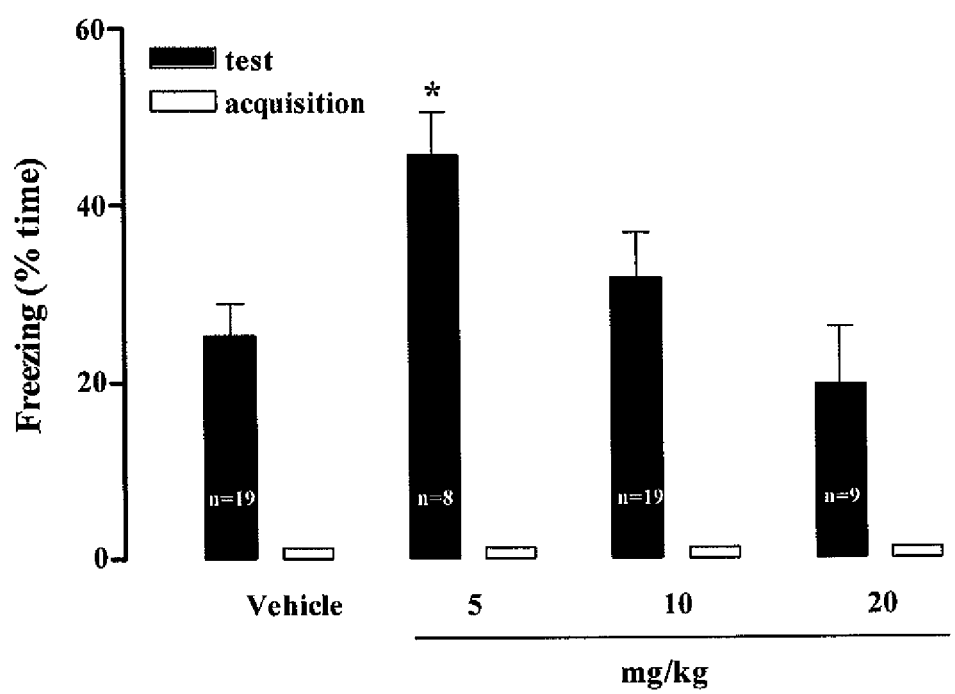

FIG. 21: Effect of 1-[2-(2,4-dimethylphenylsulfanyl)phenyl]piperazine HBr salt on contextual fear conditioning in Sprague-Dawley rats when given 1 h prior to the retention test. Freezing behaviour was scored during 58-s, prior to the foot shock US (acquisition) (white bars). Freezing behaviour was measured 24 h after the training (retention test) (black bars).

Figure 22:
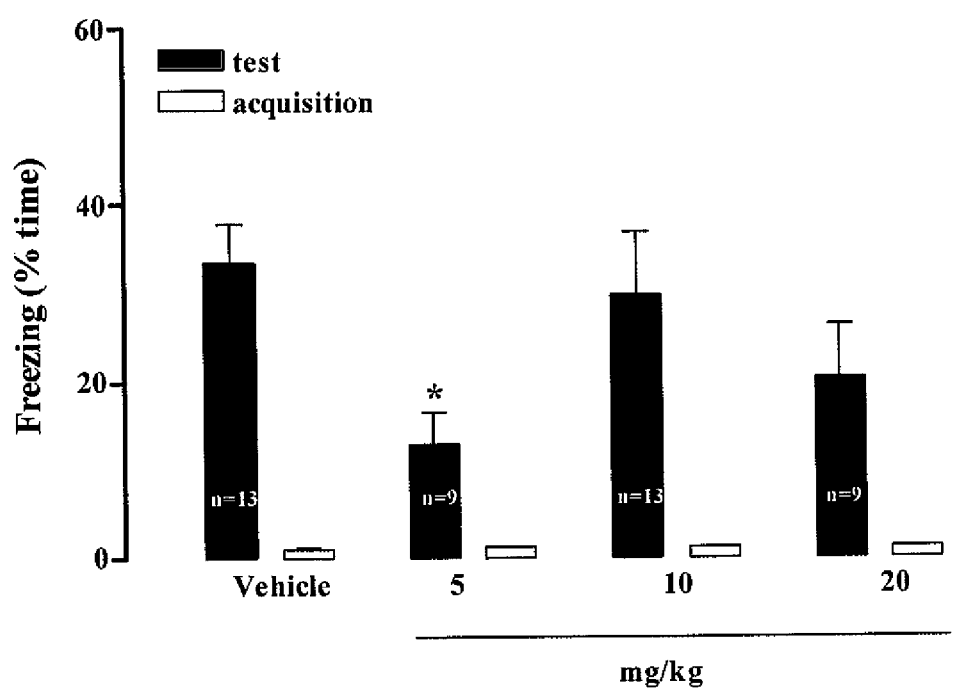

FIG. 22: Effect of 1-[2-(2,4-dimethylphenylsulfanyl)phenyl]piperazine HBr salt on contextual fear conditioning in Sprague-Dawley rats when given immediately after the acquisition. Freezing behaviour was scored during 58-s, prior to the foot shock US (pre-sock acquisition) (white bars). Freezing behaviour was measured 24 h after the training (retention test) (black bars).

Figure 23:
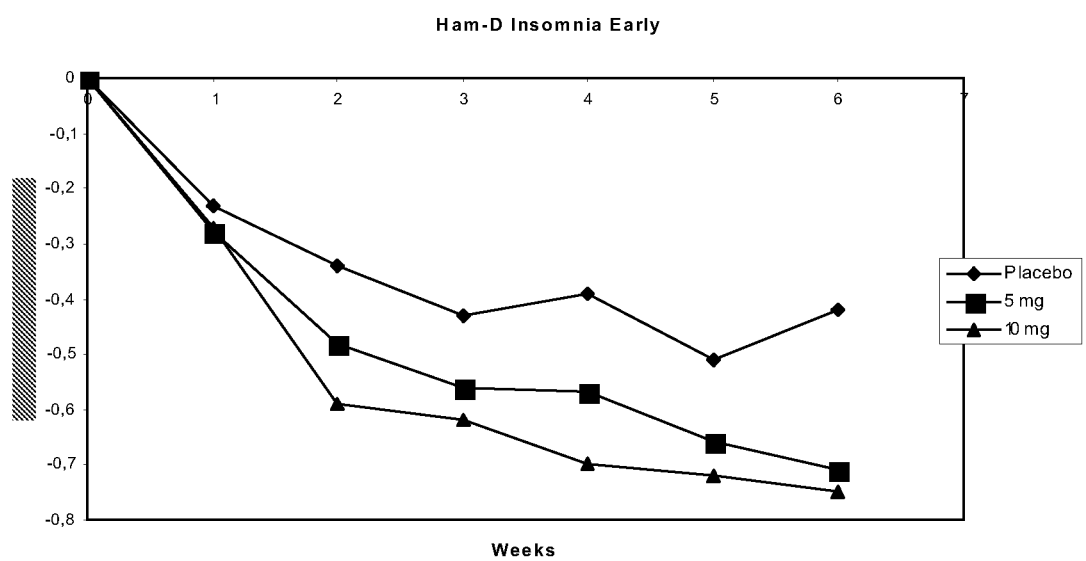
Figure 24:
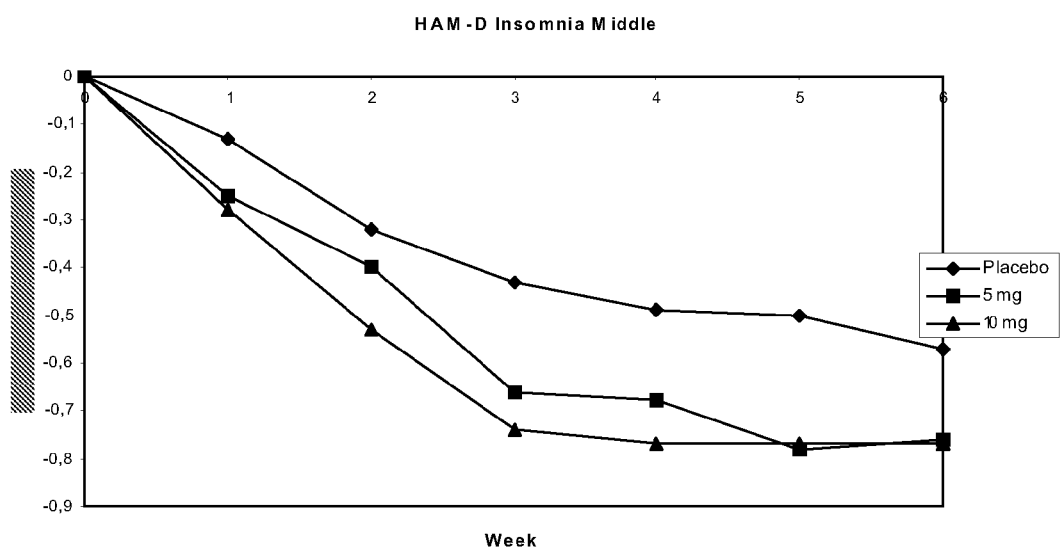
Figure 25:
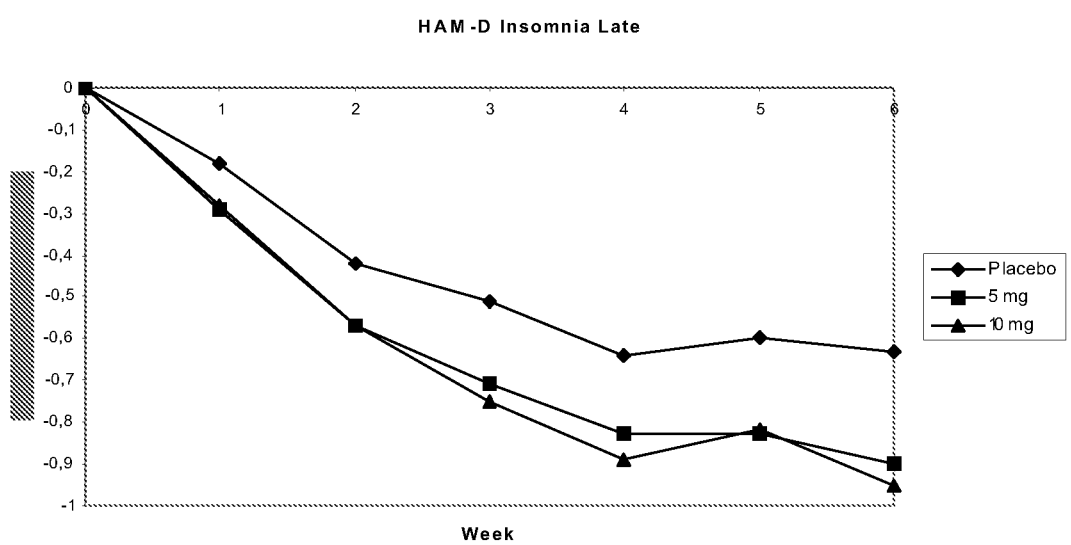

FIG. 23: Change in the HAM-D rating item 4 (Insomnia Early) for placebo, 5 mg and 10 mg compound I (HBr salt) over 6 weeks. There was approximately 100 patients in each group FIG. 24: Change in the HAM-D rating item 5 (Insomnia Middle) for placebo, 5 mg and 10 mg compound I (HBr salt) over 6 weeks. There was approximately 100 patients in each group FIG. 25: Change in the HAM-D rating item 6 (Insomnia Late) for placebo, 5 mg and 10 mg compound I (HBr salt) over 6 weeks. There was approximately 100 patients in each group.

Figure 26:
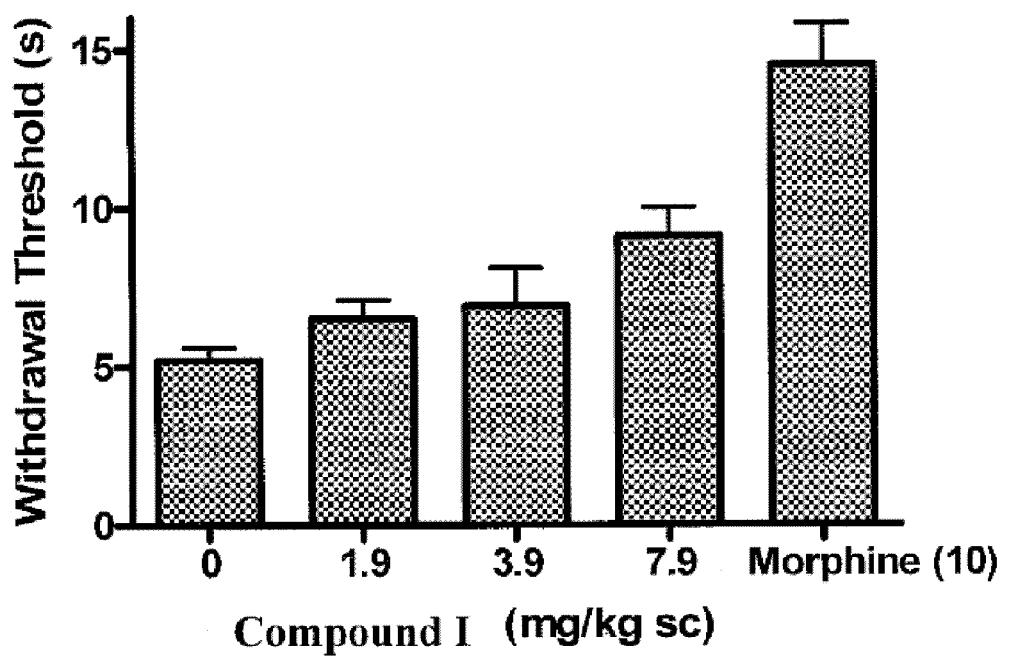

FIG. 26: Effect of compound I on withdrawal threshold in a rat chronic constriction injury model

DETAILED DESCRIPTION OF THE INVENTION

The invention relates to the use of 1-[2-(2,4-dimethylphenylsulfanyl)-phenyl]piperazine and pharmaceutically acceptable acid addition salts thereof (compound I). The structure of 1-[2-(2,4-dimethylphenylsulfanyl)-phenyl]piperazine is

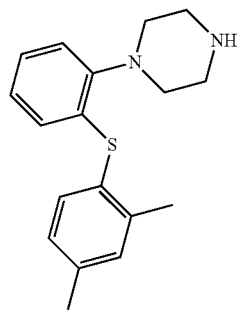 [SMILES: Cc1ccc(Sc2ccccc2N2CCNCC2)c(C)c1]

In one embodiment, said pharmaceutically acceptable acid addition salts are acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene-sulfonic, theophylline acetic acids, as well as the 8-halotheophyllines, for example 8-bromotheophylline. Said salts may also be made from inorganic salts, such as hydrochloric, hydrobromic, sulfuric, sulfamic, phosphoric and nitric acids. Particular mentioning is made of salts made from methanesulfonic acid, maleic acid, fumaric acid, meso-tartaric acid, (+)-tartaric acid, (−)-tartaric acid, hydrochloric acid, hydrobromic acid, sulphuric acid, phosphorous acid and nitric acid. Distinct mentioning is made of the hydrobromide salt.

Oral dosage forms, and in particular tablets, are often preferred by the patients and the medical practitioner due to the ease of administration and the consequent better compliance. For tablets, it is preferable that the active ingredients are crystalline. In one embodiment, the compound I is crystalline.

In one embodiment the crystals used in the present invention are solvates, i.e. crystals wherein solvent molecules from part of the crystal structure. The solvate may be formed from water, in which case the solvates are often referred to as hydrates. Alternatively, the solvates may be formed from other solvents, such as e.g. ethanol, acetone, or ethyl acetate. The exact amount of solvate often depends on the conditions. For instance, hydrates will typically loose water as the temperature is increased or as the relative humidity is decreased.

In one embodiment, the compound I is an unsolvated crystal.

Some compounds are hygroscopic, i.e. the absorb water when exposed to humidity. Hygroscopicity is generally regarded as an undesired property for compounds that are to be presented in a pharmaceutical formulation, in particular in a dry formulation, such as tablets. In one embodiment, the invention provides the use of crystals with low hygroscopicity. For oral dosage forms using crystalline active ingredients it is also beneficial if said crystals are well-defined. In the present context, the term "well-defined" in particular means that the stoichiometry is well-defined, i.e. that the ratio between the ions forming the salt is the ratio between small integers, such as 1:1, 1:2, 2:1, 1:1:1, etc. In one embodiment, the compound I forms well-defined crystals.

The crystalline compound I may exist in more than one form, i.e. they may exist in polymorphic forms. Polymorphic forms exist if a compound can crystallize in more than one form. The present invention is intended to encompass all such polymorphic forms, either as pure compounds or as mixtures thereof.

In one embodiment, the compounds of the present invention are in a purified form. The term "purified form" is intended to indicate that the compound is essentially free of other compounds or other forms of the same compound, as the case may be.

In one embodiment, the invention provides the use of crystalline salts of compound I with XRDP as shown in FIGS. 1-17, and in particular FIGS. 2, 3, 4 and 5.

The table below shows the major XRDP reflections for compound I.

Selected X-Ray Peak Positions (°2θ), all Values +−0.1°

| Crystalline base | 11.10 | 16.88 | 17.42 | 22.23 |
|---|---|---|---|---|
| -hydrobromide (α) | 5.85 | 9.30 | 17.49 | 18.58 |
| -hydrobromide (β) | 6.89 | 9.73 | 13.78 | 14.62 |
| -hydrobromide (γ) | 11.82 | 16.01 | 17.22 | 18.84 |
| -hydrobromide (hydrate) | 10.69 | 11.66 | 15.40 | 17.86 |
| -hydrobromide (ethylacetate solvate) | 8.29 | 13.01 | 13.39 | 16.62 |
| -hydrochloride | 9.41 | 12.37 | 19.66 | 22.55 |
| -hydrochloride (monohydrate) | 7.72 | 13.45 | 15.39 | 17.10 |
| -mesylate | 8.93 | 13.39 | 15.22 | 17.09 |
| -hydrogenfumarate | 5.08 | 11.32 | 17.12 | 18.04 |
| -hydrogenmaleate | 9.72 | 13.19 | 14.72 | 17.88 |
| -mesohydrogentartrate | 9.51 | 10.17 | 16.10 | 25.58 |
| -L-(+)-hydrogentartrate | 13.32 | 13.65 | 14.41 | 15.80 |
| -D-(−)-hydrogentartrate | 13.32 | 13.65 | 14.41 | 15.80 |
| -hydrogen sulphate | 11.82 | 17.22 | 17.72 | 20.13 |
| -dihydrogenphosphate | 7.91 | 11.83 | 15.69 | 17.24 |
| -nitrate | 12.50 | 17.41 | 18.12 | 18.47 |

As evidenced e.g. by FIGS. 2-5, compounds of the present invention, in casu the hydrobromide salt, may exist in several forms, i.e. be polymorphic. The polymorphic forms have different properties as shown in the examples. The beta form of the hydrobromide salt is the more stable as demonstrated by the higher DSC melting point and the lower solubility. Moreover, the beta form has an attractive combination of low hygroscopicity and solubility, which makes this compound particular suited for making tablets. Hence, in one embodiment, the invention provides the hydrobromide salt of 1-[2-(2,4-dimethylphenylsulphanyl)-phenyl]piperazine with XRDP reflections at approximately 6.89, 9.73, 13.78 and 14.62 (°2θ), and in particular with an XRPD as shown in FIG. 3.

The solubility of an active ingredient is also of significance for the choice of dosage form as it may have a direct impact on bio-availability. For oral dosage forms, a higher solubility of the active ingredient is generally believed to be beneficial as it increases the bio-availability.

The pharmacological profile of compound I is provided in the examples, but may be summarised as follows. Compound I is an inhibitor of the serotonin transporter, it antagonises the serotonin receptor 3 (5-HT$_3$) and it is a partial agonist of the serotonin receptor 1A (5-HT$_{1A}$).

The data reported in examples 14 and 17 show that compound I is useful in the treatment of pain, and that they may even have an analgesic effect.

In one embodiment said pain is chronic pain including phantom limb pain, neuropathic pain, diabetic neuropathy, post-herpetic neuralgia (PHN), carpal tunnel syndrome (CTS), HIV neuropathy, complex regional pain syndrome (CPRS), trigeminus neuralgia, tic douloureux, surgical intervention (e.g. post-operative analgesics), diabetic vasculopathy, capillary resistance, diabetic symptoms associated with insulitis, pain associated with menstruation, pain associated with cancer, dental pain, headache, migraine, tension-type headache, trigeminal neuralgia, temporomandibular joint syndrome, myofascial pain, muscular injury, fibromyalgia syndrome, bone and joint pain (osteoarthritis), rheumatoid arthritis, rheumatoid arthritis and edema resulting from trauma associated with burns, strains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain or geriatric pain. In one embodiment, pain is irritable bowl syndrome (IBS).

A fraction of patients with major depressive disorder will respond to treatment with e.g. SSRI in the sense that they will improve on clinically relevant scales, such as HAMD or MADRS, but where other symptoms, such as cognitive and/or sleep symptoms remain. In the present context, these patient are referred to as suffering from depression with residual symptoms.

Cognitive symptoms include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive symptoms may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts.

As shown in example 15, compound I gives rise to an increase in the extra-cellular level of acetylcholine in the prefrontal cortex and the ventral hippocampus in rats. These pre-clinical findings are expected to translate into a clinical effect in the treatment of cognitive impairments, cf. the use of acetylcholine esterase inhibitors in the treatment of cognitive impairments, e.g. in Alzheimer's disease. Further support to this position can be found in example 16, wherein data show that compound I enhances contextual memory in rats. All in all, the effects on acetylcholine levels and memory in rats strongly suggest that compound I has a beneficial effect on cognitive impairment. Hence, compound I is believed to be particularly useful in the treatment of depression with residual symptoms, in particular with residual symptoms related to cognition.

Compound I has been tested in clinical trials in patients using HAM-D (Hamilton Rating Scale for Depression) as clinical end-point. The HAM-D scale may be used to assess the severity of depression in patients by means of a 24 items questionnaire. Item 4, 5 and 6 of the scale relate to how the patients sleep, i.e. is it easy to fall asleep (insomnia Early), does the patient wake up during the night (Insomnia Middle), and does the patient wake up early in the morning (Insomnia Late). The compound was tested at 5 and 10 mg daily against placebo with approximately 100 patients per arm. The data in FIGS. 23-25 clearly show that compound I gives rise to a large and dose dependent improvement of the sleep pattern which is superior to that provided by placebo. Hence, compound I is believed to be particularly useful in the treatment of depression with residual symptoms, in particular residual symptoms related to sleep.

It is well-known that sleep disturbances is a general adverse affect of most antidepressants. In particular SSRI's and compounds which inhibit the noradrenaline transporter are reported to give rise to problems with sleep initiation and maintenance and problems with insomnia are also often reported [*Int. Clin. Psychpharm.,* 21 (suppl 1), S25-S29, 2006]. Others report that such compounds give rise to suppressed REM sleep, increased sleep latency, less efficient sleep, increase in nocturnal awakenings, and fragmentation of sleep [*Hum. Psychopharm. Clin. Exp.*, 20, 533-559, 2005]. It is therefore a surprising result that the administration of compound I is not associated with adverse sleep effects, but in fact provides an improvement of the sleep pattern.

It is well know that treatment with anti-depressants in general and SSRI's in particular may be associated with sexual dysfunction, which frequently leads to discontinuation of the treatment. As much as 30-70% of patients on SSRIs report deficits in sexual function [*J. Clin. Psych.*, 66, 844-848, 2005], which deficits include decreased libido, delayed, reduced or absent orgasms, diminished arousal, and erectile dysfunction.

A total of 114 healthy subjects have been exposed to compound I in clinical trials; of these 114 subjects, only one subject reported sexual dysfunction. These data suggest that clinical intervention using compound I is associated with surprisingly few deficits in sexual functioning.

This notion was further supported by clinical trials conducted in patients. The above mentioned clinical trial in patients also captured sexual adverse effects reported by the patients. The table below shows the number of patients reporting the specified types of sexually related adverse effects.

| Adverse effect reported | Placebo | 5 mg | 10 mg |
|---|---|---|---|
| Anorgasmia | 0 | 0 | 0 |
| Ejaculation delayed | 0 | 0 | 0 |
| Erectile dysfunction | 0 | 0 | 0 |
| Libido decreased | 0 | 1 | 1 |
| Orgasm abnormal | 2 | 0 | 0 |
| Loss of libido | 0 | 1 | 0 |
| Orgasmic sensation decreased | 0 | 0 | 0 |

The above results which show that the sexual adverse effect of compound I is similar to placebo and thus much better than what would normally be expected from a antidepressant, and in particular an SSRI. Hence, a clinical intervention comprising the administration of compound I is believed to be particular beneficial to the patient in that sexually related adverse events are diminished (or even absent) compared to a clinical intervention comprising the administration of an SSRI.

In one embodiment, the invention relates to a method for the treatment of pain or residual symptoms in depression, the method comprising the administration of a therapeutically effective amount of 1-[2-(2,4-dimethylphenylsulfanyl)phenyl]-piperazine and pharmaceutically acceptable acid addition salts thereof (compound I) to a patient in need thereof. In one embodiment, said patient has been diagnosed with the above mentioned diseases.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "a therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspects of the invention. The patient to be treated is preferably a mammal, in particular a human being.

Typically, the treatment of the present invention will involve daily administration of compound I. This may involve once daily administration, or administration twice a day or even more frequently.

In one embodiment, the invention relates to the use of 1-[2-(2,4-dimethylphenylsulfanyl)phenyl]piperazine and pharmaceutically acceptable acid addition salts thereof (compound I) in the manufacture of a medicament for the treatment of pain or residual symptoms in depression.

In one embodiment, the invention relates to 1-[2-(2,4-dimethylphenyl-sulfanyl)phenyl]piperazine and pharmaceutically acceptable acid addition salts thereof (compound I) for use in the treatment of pain or residual symptoms in depression.

The pharmaceutical formulations of the invention may be prepared by conventional methods in the art. Particular mentioning is made of tablets, which may be prepared by mixing the active ingredient with ordinary adjuvants and/or diluents and subsequently compressing the mixture in a conventional tabletting machine. Examples of adjuvants or diluents comprise: anhydrous calcium hydrogen phosphate, PVP, PVP-VA co-polymers, microcrystalline cellulose, sodium starch glycolate, corn starch, mannitol, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, compound I is administered in unit dosage form containing said compounds in an amount of about 1 to 50 mg. An upper limit is believed to be set by the concentration dependency of the 5-HT$_3$ activity. The total daily dose is usually in the range of about 1-20 mg, such as about 1 to 10 mg, about 5-10 mg, about 10-20 mg, or about 10-15 mg of the compound of the invention. Particular mentioning is made of daily doses of 1, 2.5, 5, 10, 15 or 20 mg.

Tablets comprising compound I may conveniently be prepared by wet granulation. Using this method, the dry solids (active ingredients, filler, binder etc.) are blended and moistened with water or another wetting agent (e.g. an alcohol) and agglomerates or granules are built up of the moistened solids. Wet massing is continued until a desired homogenous particle size has been achieved whereupon the granulated product is dried. Compound I is typically mixed with lactose monohydrate, corn starch and copovidone in a high shear mixer together with water. Following formation of granulates, these granulates may be sieved in a sieve with a suitable sieve size, and dried. The resulting, dried granulates are then mixed with microcrystalline cellulose, croscarmellose sodium and magnesium stearate, following which the tablets are pressed. Alternatively, wet granulation of compound I may be achieved using mannitol, corn starch and copovidone, which granulates are mixed with microcrystalline cellulose, sodium starch glycolate and magnesium stearate before tablets are pressed. Alternatively, wet granulation of the compounds of the present invention may be achieved by using anhydrous calcium hydrogen phosphate, corn starch and copovidone, which granulates are mixed with microcrystalline cellulose, sodium starch glycolate (type A), talc and magnesium stearate before tablets are pressed. Copovidone is a PVP-VA copolymer.

The free base of the compound I may be prepared as disclosed in WO 2003/029232. Salts of the present invention may be prepared by dissolving the free base in an appropriate solvent, adding the relevant acid, followed by precipitation. Precipitation may be accomplished either by the addition of a second solvent, and/or evaporation, and/or cooling. Alternatively, the free base of the present invention and ultimately the compounds of the present invention may be synthesised in a palladium catalysed reaction as described WO 2007/144005.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods $^1$H NMR spectra are recorded at 500.13 MHz on a Bruker Avance DRX500 instrument. Dimethyl sulfoxide (99.8% D) is used as solvent, and tetramethylsilane (TMS) is used as internal reference standard.

The melting points are measured using Differential Scanning Calorimetry (DSC). The equipment is a TA-Instruments DSC-Q1000 calibrated at 5°/min to give the melting point as onset value. About 2 mg of sample is heated 5°/min in a loosely closed pan under nitrogen flow.

Thermo gravimetric analysis (TGA) used for estimation of solvent/water content of dried material is performed using a TA-instruments TGA-Q500. 1-10 mg sample is heated 10°/min in an open pan under nitrogen flow.

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector.

Example 1

In Vitro Receptor Pharmacology

Rat serotonin transporter: IC$_{50}$ 5.3 nM (blockade of 5-HT uptake)

Human serotonin transporter: IC$_{50}$ 40 nM (blockade of 5-HT uptake)

Human 5-HT$_{1A}$ receptor: K$_i$ 40 nM with partial agonism (efficacy 85%)

Rat 5-HT$_3$ receptor: IC$_{50}$ 0.2 nM (antagonism in functional assay)

Human 5-HT$_{3A}$ receptor: IC$_{50}$ around 20 nM (antagonism in functional assay). At higher concentration, the compound exhibits agonistic activity with an ED$_{50}$ of 2.1 µM. The compound of the invention also showed high affinity for the human 5HT3 receptor in an in vitro binding assay (Ki 4.5 nM).

Example 2a

Preparation of the Free Base of Compound I 10 grams of 1-[2-(2,4-Dimethylphenylsulfanyl)-phenyl]piperazine hydrobromide was treated with a stirred mixture of 100 ml 3 M NaOH and 100 ml ethyl acetate for 10 minutes. The organic phase was separated, washed with 100 ml 15%-wt NaCl (aq), dried over MgSO$_4$, filtered and concentrated in vacuum producing 7.7 gram (98%) of compound I base as a clear colourless oil.

NMR complies with structure.

Example 2b

Preparation of Crystalline Base of Compound I 3.0 gram of 1-[2-(2,4-Dimethylphenylsulfanyl)-phenyl]piperazine colourless oil was treated with 70 ml acetonitrile and heated to reflux. The almost clear solution was filtered and the clear filtrate was cooled spontaneously upon which precipitation began shortly after filtration. The mixture was stirred at room temperature (22° C.) for 2 hours and the product was isolated by filtration and dried in vacuum (40° C.) overnight. The crystalline base was isolated as a white solid in 2.7 gram (90%). NMR complies with structure. Elemental analysis: 72.40%; C, 9.28%; N, 7.58%; H. (theory: 72.26%; C, 9.36%; N, 7.42%; H).

Example 2c

Characterisation of Crystalline Base of Compound I

The base, as prepared in example 2b, is crystalline (XRPD)—see FIG. 1. It has a melting point of ~117° C. It is not hygroscopic and has a solubility of 0.1 mg/ml in water.

Example 3a

Preparation of the Alpha Form of the Hydrobromide Salt of Compound I 2.0 gram of 1-[2-(2,4-Dimethylphenylsulfanyl)-phenyl]piperazine was dissolved in hot 30 ml ethyl acetate and added 0.73 ml 48%-wt HBr (aq). This addition caused formation of a thick slurry and additional 10 ml ethyl acetate was added in order to have proper stirring. The slurry was stirred at room temperature for one hour. Filtration and drying in vacuum (20° C.) over night produced 2.0 gram of the product as a white solid (80%). NMR complies with structure. Elemental analysis: 57.05%; C, 7.18%; N, 6.16%; H. (Theory for 1:1 salt: 56.99%; C, 7.39%; N, 6.11%; H).

Example 3b

Characterisation of the Alpha Form of the Hydrobromide of Compound I

The alpha form of the hydrobromide, as prepared in example 3a, is crystalline (XRPD)—see FIG. 2. It has a melting point of ~226° C. It absorbs about 0.3% of water when exposed to high relative humidity and has a solubility of 2 mg/ml in water.

Example 3c

Preparation of the Beta Form of the Hydrobromide Salt of Compound I 49.5 gram of 1-[2-(2,4-Dimethylphenylsulfanyl)-phenyl]piperazine colourless oil was dissolved in 500 ml ethyl acetate and added 18.5 ml 48%-wt HBr (aq). This addition caused formation of a thick slurry which was stirred over night at room temperature.
Filtration and drying in vacuum (50° C.) over night produced the product in 29.6 gram as white solid (47%).
NMR complies with structure. Elemental analysis: 56.86%; C, 7.35%; N, 6.24%; H. (Theory for 1:1 salt: 56.99%; C, 7.39%; N, 6.11%; H).

Example 3d

Characterisation of the Beta Form of the Hydrobromide of Compound I

The beta form of the hydrobromide, as prepared in example 3c, is crystalline (XRPD) see FIG. 3. It has a melting point of ~231° C. It absorbs about 0.6% of water when exposed to high relative humidity and has a solubility of 1.2 mg/ml in water.

Example 3e

Preparation of the Gamma Form of the Hydrobromide Salt of Compound I 1 g of 1-[2-(2,4-Dimethylphenylsulfanyl)-phenyl]piperazine hydrobromide as prepared in example 4a was added 20 ml water and heated to 85° C. The solution was almost clear. Addition of 1 drop of HBr made it clear. HBr was added until cloud point was observed. The solution was cooled to room temperature and dried. NMR complies with structure. Elemental analysis: 56.63%; C, 7.18%; N, 6.21%; H. (Theory for 1:1 salt: 56.99%; C, 7.39%; N, 6.11%; H).

Example 3f

Characterisation of the Gamma Form of the Hydrobromide of Compound I

The hydrobromide, as prepared in example 3e, is crystalline (XRPD)—see FIG. 4. The DSC curve shows some thermal events at about 100° C.; probably change in crystal form. Then it melts at about 220° C. It absorbs about 4.5% of water when exposed to high relative humidity and at 30% RH at room temperature about 2% of water is absorbed.

Example 3g

Preparation of the Hydrobromide Hydrate of Compound I 1.4 gram of 1-[2-(2,4-Dimethylphenylsulfanyl)-phenyl]piperazine oil was added 20 ml water, and heated to 60° C. pH was adjusted to 1 using 48% HBr. The solution was cooled to room temperature and dried. NMR complies with structure. Elemental analysis: 55.21%; C, 7.16%; N, 6.34%; H. (Theory for 1:1 salt hemihydrate: 55.68%; C, 7.21%; N, 6.23%; H).

Example 3h

Characterisation of the Hemi Hydrate of the Hydrobromide of Compound I

The hydrate as prepared in Example 3g is crystalline (XRPD)—see FIG. 5.
The water content depends strongly on the relative humidity. At room temperature and 95% RH the water content is about 3.7%. Dehydration occurs by heating to about 100° C.

Example 3i

Preparation of the Ethyl Acetate Solvate of the Hydrobromide Salt of Compound I 0.9 gram of 1-[2-(2,4-Dimethylphenylsulfanyl)-phenyl]piperazine oil was dissolved in 35 ml ethyl acetate and added 0.5 ml 48%-wt HBr (aq). This addition caused formation of an thick slurry which was stirred over night at room temperature. Filtration and washing with 30 ml diethyl ether followed by drying in vacuum (50° C.) over night produced 1-[2-(2,4-Dimethylphenylsulfanyl)-phenyl]piperazine HBr EtOAc solvate in 1.0 gram (65%). NMR complies with structure. Elemental analysis: 56.19%; C, 6.60%; N, 6.56% H. (Theory for 1:1 salt when corrected for 8% of Ethyl acetate and 0.5% water as determined by TGA and KF: 56.51%; C, 6.76%; N, 6.38%; H).

Example 3j

Characterisation of the Ethyl Acetate Solvate of the Hydrobromide of Compound I

The ethyl acetate solvate, as prepared in example 3i, is crystalline (XRPD)—see FIG. 6. The batch contains a mixture of the solvate and the alpha form of compound I, probably because the drying has caused partly desolvation. The desolvation starts at ~75° C. when heated 10°/min. After desolvation the alpha form is formed. If exposed to high relative humidity, the ethyl acetate is replaced by water, which is released when the humidity subsequently is lowered. The resulting solid is hygroscopic and absorbs 3.2% of water at high relative humidity.

Example 4a

Preparation of Hydrochloride Salt of Compound I 1.0 gram of 1-[2-(2,4-Dimethylphenylsulfanyl)-phenyl]piperazine oil was dissolved in 20 ml ethyl acetate using gentle heating (30° C.). When a clear solution was obtained a solution of 2 M HCl in diethyl ether was added slowly until pH was approximately 1-2. During the addition spontaneous precipitation was observed. After final addition the suspension was stirred for 1 hour before the white precipitate was isolated by filtration and dried in vacuum (40° C.) overnight. 1-[2-(2,4-Dimethylphenylsulfanyl)-phenyl]piperazine hydrochloride was isolated in 1.1 gram (99%).

NMR complies with structure. Elemental analysis: 64.18%; C, 8.25%; N, 6.96%; H. (Theory for 1:1 salt when corrected for 0.66% of water as determined by TGA: 64.13%; C, 8.31%; N, 6.95%; H).

Example 4b

Characterisation of the Hydrochloride of Compound I

Figure 7:
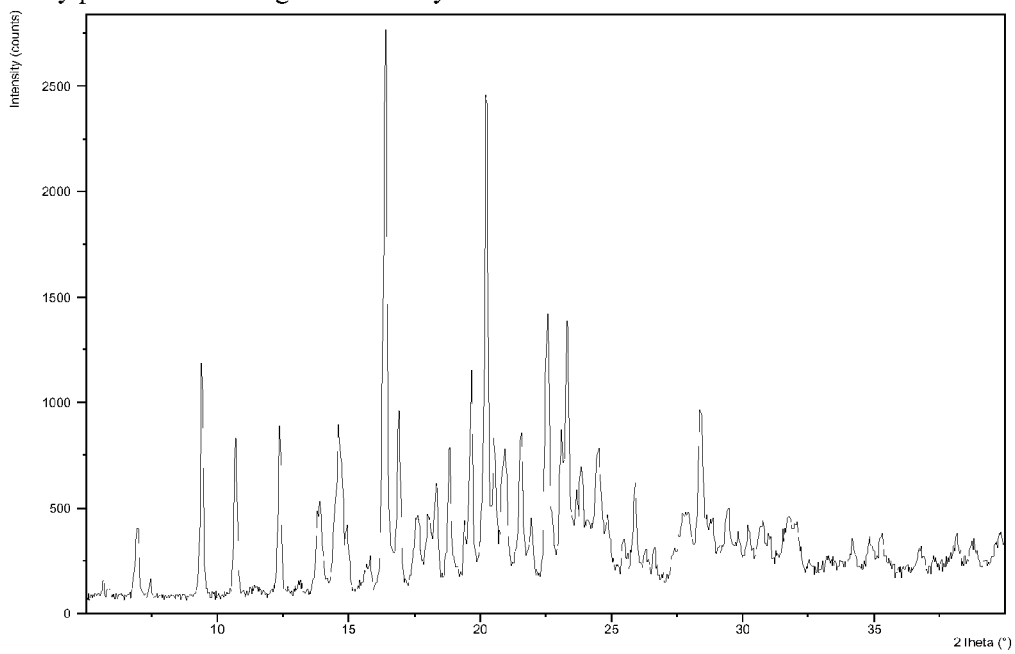

The hydrochloride, as prepared in example 4a, is crystalline (XRPD)—see FIG. 7. It has a melting point of ~236° C. It absorbs about 1.5% of water when exposed to high relative humidity and has a solubility of 3 mg/ml in water.

Example 4c

Preparation of the Hydrochloride Monohydrate of Compound I 11.9 gram of 1-[2-(2,4-Dimethylphenylsulfanyl)-phenyl]piperazine oil was dissolved in 100 ml ethanol using heating. When a homogenous solution was obtained addition of 3.5 ml conc. HCl (aq) took place causing the immediately precipitation of a white solid. The suspension was stirred for 5 minutes at first and then on ice-bath another hour before filtration. The white solid was washed using 100 ml of fresh cool ethanol (placed in freezer at −18° C. for 2 hours), 50 ml acetone and finally 50 ml diethyl ether before dried in vacuum (50° C.) overnight. 1-[2-(2,4-Dimethylphenylsulfanyl)-phenyl]piperazine HCl was isolated in 5.1 gram (38%).

NMR complies with structure. Elemental analysis: 61.23%; C, 7.91%; N, 7.16%; H. (Theory for 1:1 salt monohydrate: 61.26%; C, 7.94%; N, 7.14% H).

Example 4d

Characterisation of the Hydrochloride Monohydrate of Compound I

Figure 8:
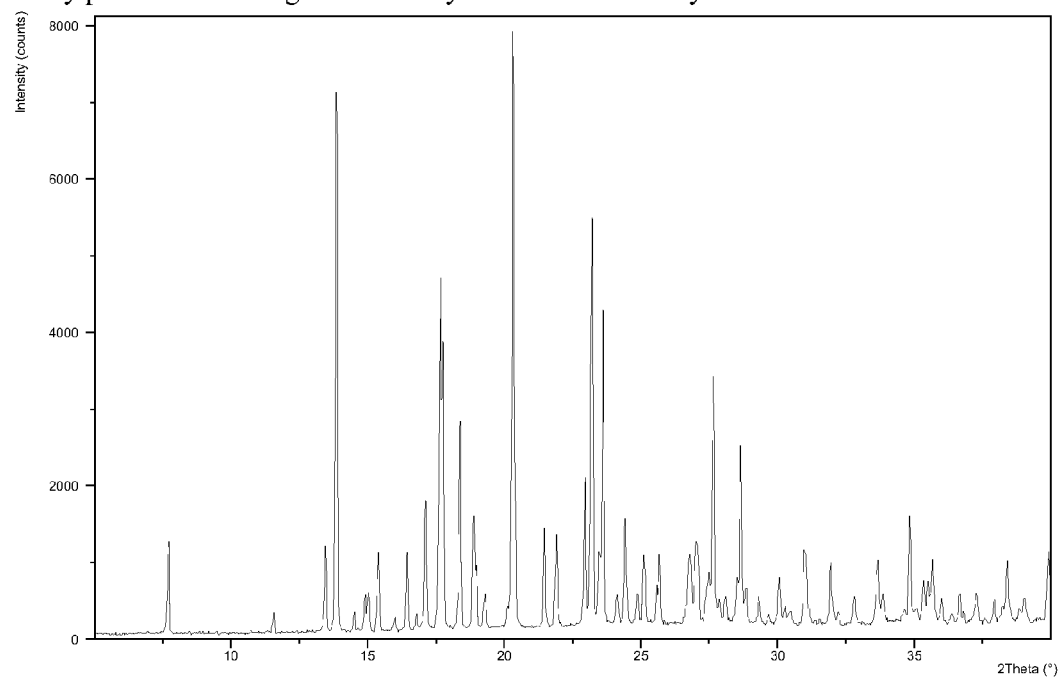

The hydrochloride monohydrate, as prepared in example 4c, is crystalline (XRPD)—see FIG. 8. It dehydrates starting at about 50° C. Some thermal events, probably rearrangement, occur by further heating, and it melts at about 230° C. followed by recrystallisation and melting at about 236° C. It does not absorb further amount of water when exposed to high relative humidity and the hydrate bounded water is not released until the relative humidity is decreased to below 10% RH at room temperature. It has a solubility of about 2 mg/ml in water.

Example 5a

Preparation of Mesylate Salt of Compound I 1.0 gram of 1-[2-(2,4-Dimethylphenylsulfanyl)-phenyl]piperazine oil was dissolved in 20 ml ethyl acetate by heating (70° C.). When a clear solution was obtained 0.35 gram of methane sulphonic acid (1.1 eqv.) was added slowly. After final addition the solution was cooled on ice and diethyl ether was added slowly causing the precipitation of the product. The suspension was stirred for 2 hours on ice before the white precipitate was isolated by filtration and dried in vacuum (40° C.) overnight. 1-[2-(2,4-Dimethylphenylsulfanyl)-phenyl]piperazine mesylate was isolated in 1.1 gram (85%). NMR complies with structure. Elemental analysis: 57.81%; C, 6.81%; N, 6.68%; H. (Theory for a 1:1 salt: 57.81%; C, 7.10%; N, 6.64%; H).

Example 5b

Characterisation of the Mesylate of Compound I

Figure 9:
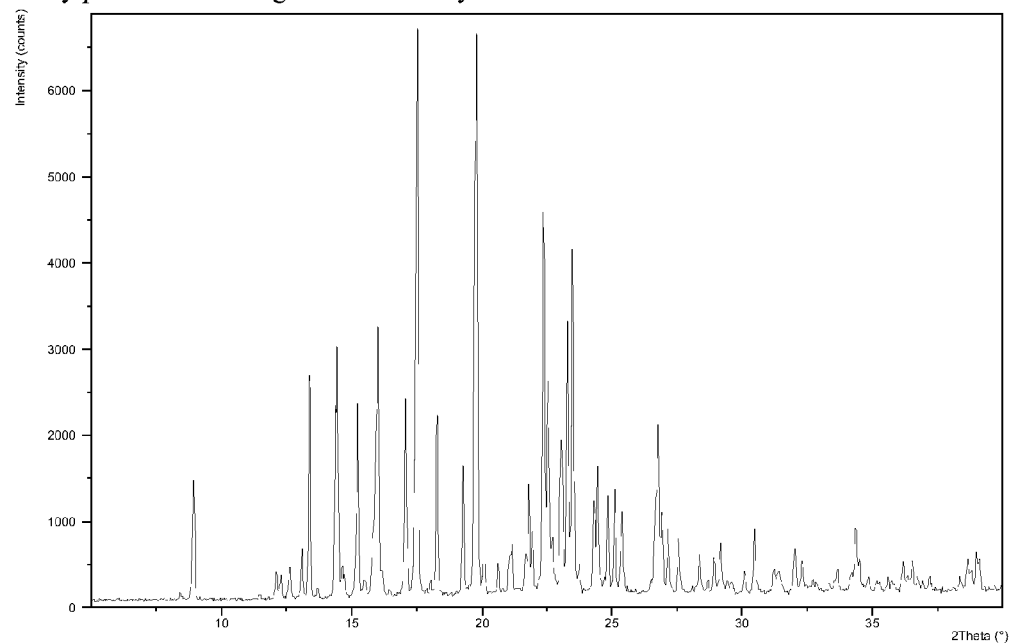

The mesylate, as prepared in example 5a, is crystalline (XRPD)—see FIG. 9. It has a melting point of ~163° C. It is hygroscopic (absorbs about 8% of water when exposed to 80% relative humidity and is thereby transformed into a hydrated form. The last 6% of the absorbed water is not released until the relative humidity is below 10% RH. It has a very high solubility in water (>45 mg/ml).

Example 6a

Preparation of Fumarate of Compound I 5.5 gram 1-[2-(2,4-Dimethylphenylsulfanyl)-phenyl]piperazine oil was heated to reflux in a mixture of 50 ml methanol and 50 ml ethyl acetate. The solution was left to cool slightly before addition of 2.1 gram fumaric acid took place causing an exothermic reaction and precipitation of a white solid. The suspension was stirred while being allowed to cool to room temperature followed by 2 hours in the freezer at −18° C. The white solid was collected by filtration and washed with 20 ml cold ethyl acetate before drying in vacuum (50° C.) over night. The product was isolated in 3.1 gram (44%).

NMR complies with structure. Elemental analysis: 63.42%; C, 6.64%; N, 6.42%; H. (Theory for a 1:1 salt: 63.74%; C, 6.76%; N, 6.32%; H).

Example 6b

Characterisation of the Fumarate of Compound I

Figure 10:
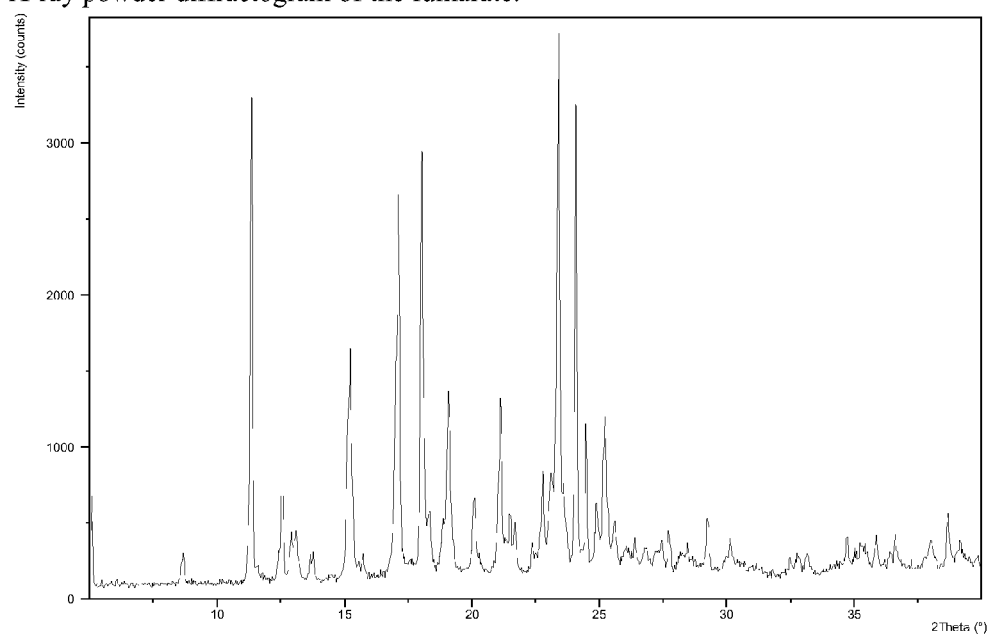

The fumarate, as prepared in example 6a, is crystalline (XRPD)—see FIG. 10. It has a melting point of ~194° C. The solubility in water is 0.4 mg/ml.

Example 7a

Preparation of Maleate of Compound I 2.5 gram 1-[2-(2,4-Dimethylphenylsulfanyl)-phenyl]piperazine oil was dissolved in 50 ml ethyl acetate and heated to 60° C. followed by addition of 1.1 gram maleic acid. The mixture was heated again to reflux for 5 minutes and left to cool to room temperature while stirring. During the cooling precipitation started and was finalized by 4 hours in the freezer (−18° C.). The white solid was collected by filtration and washed with 50 ml diethyl ether before drying in vacuum (50° C.) over night. This produced 1.3 gram of 1-[2-(2,4-Dimethylphenylsulfanyl)-phenyl]piperazine Maleate (38%) that was recrystallised by treatment with 40 ml ethyl acetate and 5 ml methanol at reflux. The clear solution was cooled to room temperature followed by 2 hours in the freezer (−18° C.) before filtering and washed twice with 10 ml cold ethyl acetate followed by drying in vacuum (50° C.) for two days. 1-[2-(2,4-Dimethylphenylsulfanyl)-phenyl]piperazine Maleate was isolated in 0.9 gram (69%).

NMR complies with structure. Elemental analysis: 63.57%; C, 6.79%; N, 6.39%; H. (Theory for a 1:1 salt: 63.74%; C, 6.76%; N, 6.32%; H).

Example 7b

Characterisation of the Maleate of Compound I

Figure 11:
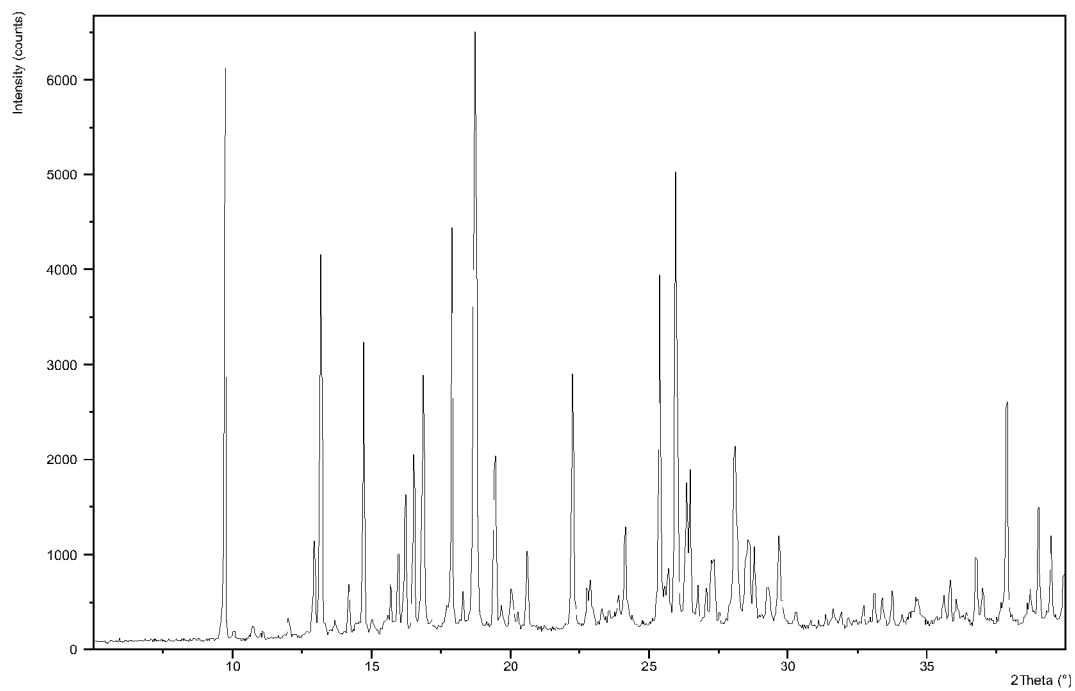

The maleate, as prepared in example 7a, is crystalline (XRPD)—see FIG. 11. It has a melting point of ~152° C. The solubility in water is ~1 mg/ml.

Example 8a

Preparation of Meso-Tartrate of Compound I 11.1 ml of a 0.30 M solution of 1-[2-(2,4-Dimethylphenylsulfanyl)-phenyl]piperazine in acetone was treated with 0.5 gram meso-tartaric acid dissolved in 5 ml acetone. The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine meso-tartaric acid was isolated in 1.4 gram (93%). NMR complies with structure. Elemental analysis: 58.58%; C, 6.29%; N, 6.40%; H. (Theory for a 1:1 salt: 58.91%; C, 6.25%; N, 6.29%; H).

Example 8b

Characterisation of the Meso-Tartrate of Compound I

Figure 12:
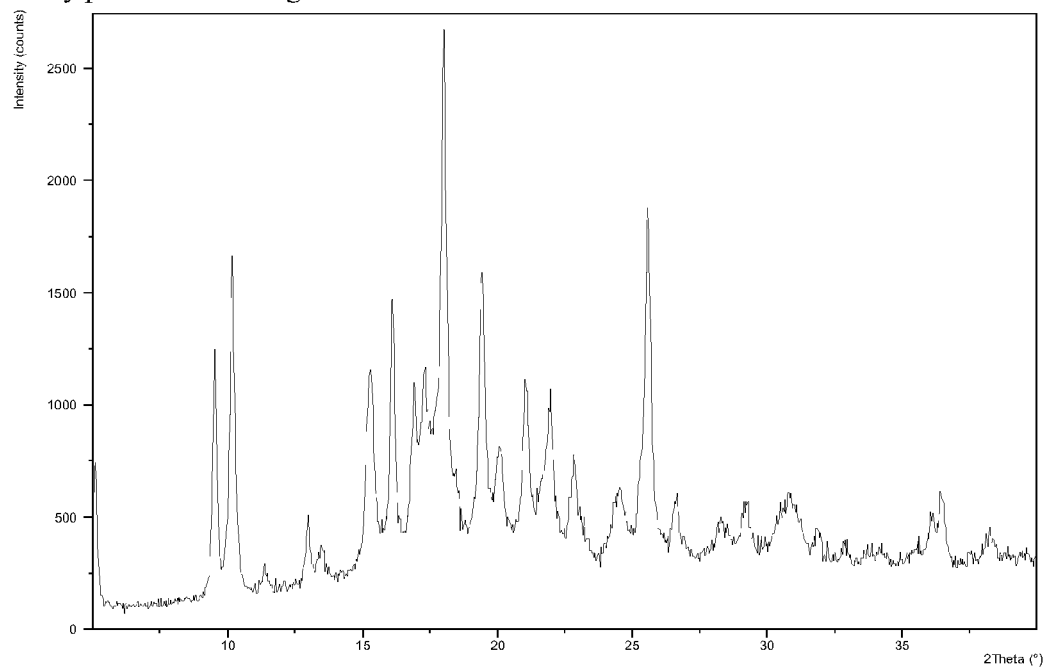

The meso-tartrate, as prepared in example 8a, is crystalline (XRPD)—see FIG. 12. It has a melting point of ~164° C. The solubility in water is ~0.7 mg/ml.

Example 9a

Preparation of L-(+)-Tartrate of Compound I 11.1 ml of a 0.30 M solution of 1-[2-(2,4-Dimethylphenylsulfanyl)-phenyl]piperazine in acetone was treated with 0.5 gram L-(+)-tartaric acid dissolved in 5 ml acetone. The mixture was stirred at room temperature for 30 minutes during which precipitation took place. Filtration and washing first with 5 ml acetone and then 3 ml diethyl ether achieved the product as a white solid that was dried in vacuum (50° C.) over night. 1-[2-(2,4-Dimethylphenylsulfanyl)-phenyl]piperazine (+)-tartaric acid was isolated in 1.2 gram (81%). NMR complies with structure. Elemental analysis: 58.86%; C, 6.30%; N, 6.38%; H. (Theory for a 1:1 salt: 58.91%; C, 6.25%; N, 6.29%; H).

Example 9b

Characterisation of the L-(+)-Tartrate of Compound I

Figure 13:
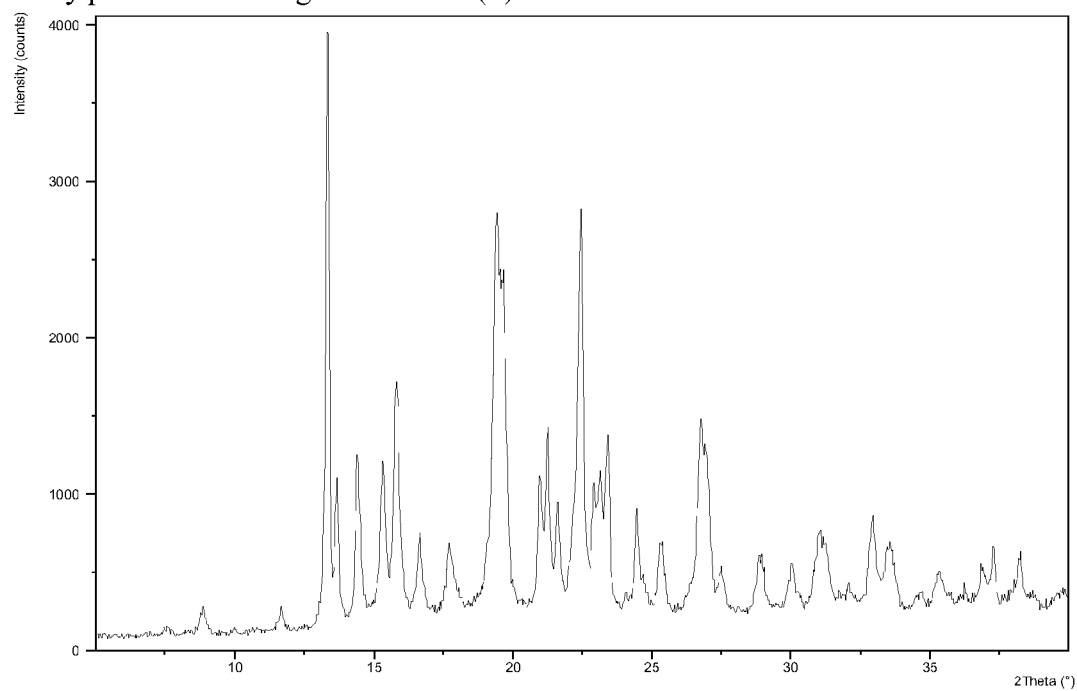

The L-(+)-tartrate, as prepared in example 9a, is crystalline (XRPD)—see FIG. 13. It has a melting point of ~171° C. The solubility in water is ~0.4 mg/ml.

Example 10a

Preparation of D-(−)-Tartrate of Compound I 11.1 ml of a 0.30 M solution of 1-[2-(2,4-Dimethylphenylsulfanyl)-phenyl]piperazine in acetone was treated with 0.5 gram D-(−)-tartaric acid dissolved in 5 ml acetone. The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine D-(−)-tartaric acid was isolated in 1.0 gram (68%). NMR complies with structure. Elemental analysis: 58.90%; C, 6.26%; N, 6.35%; H. (Theory for a 1:1 salt: 58.91%; C, 6.25%; N, 6.29%; H).

Example 10b

Characterisation of the D-(−)-Tartrate of Compound I

Figure 14:
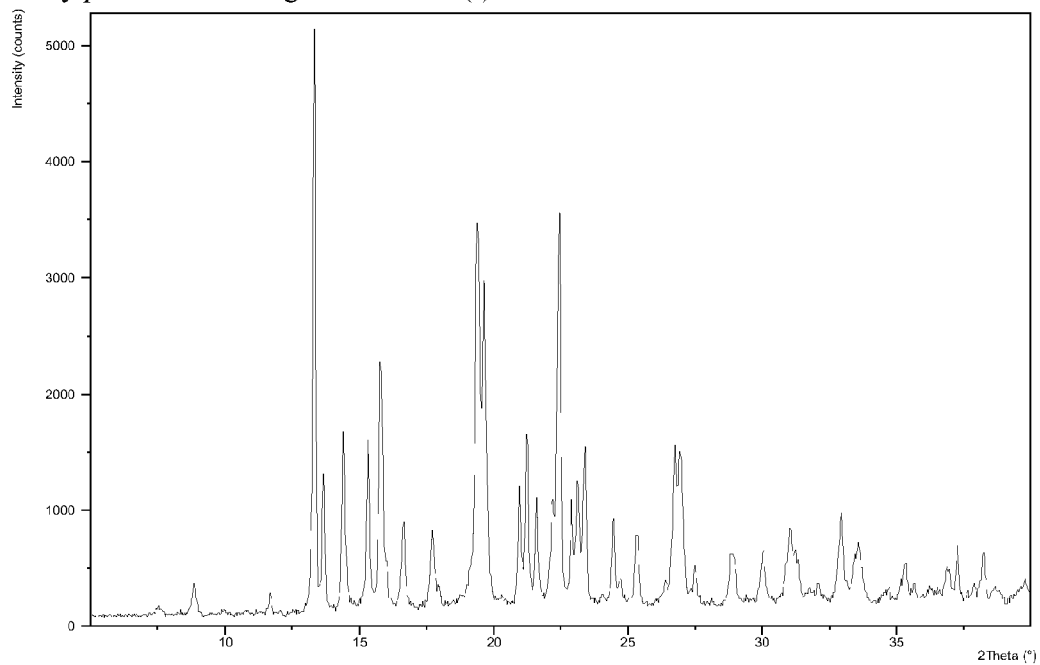

The D-(+)-tartrate, as prepared in example 10a, is crystalline (XRPD)—see FIG. 14. It has a melting point of ~175° C. The solubility in water is ~0.4 mg/ml.

Example 11a

Preparation of Sulphate of Compound I 11.1 ml of a 0.30 M solution of 1-[2-(2,4-Dimethylphenylsulfanyl)-phenyl]piperazine in acetone was treated with 2.2 ml of a 3 M solution of $H_2SO_4$ (aq). The mixture was stirred at room temperature for 30 minutes and then on ice-bath for another 4 hours before precipitation took place and was finalized. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine sulphate was isolated in 0.51 gram (39%). NMR complies with structure. Elemental analysis: 54.53%; C, 7.22%; N, 6.28%; H. (Theory for a 1:1 salt: 54.52%; C, 7.07%; N, 6.10%; H).

Example 11b

Characterisation of the Sulphate of Compound I

Figure 15:
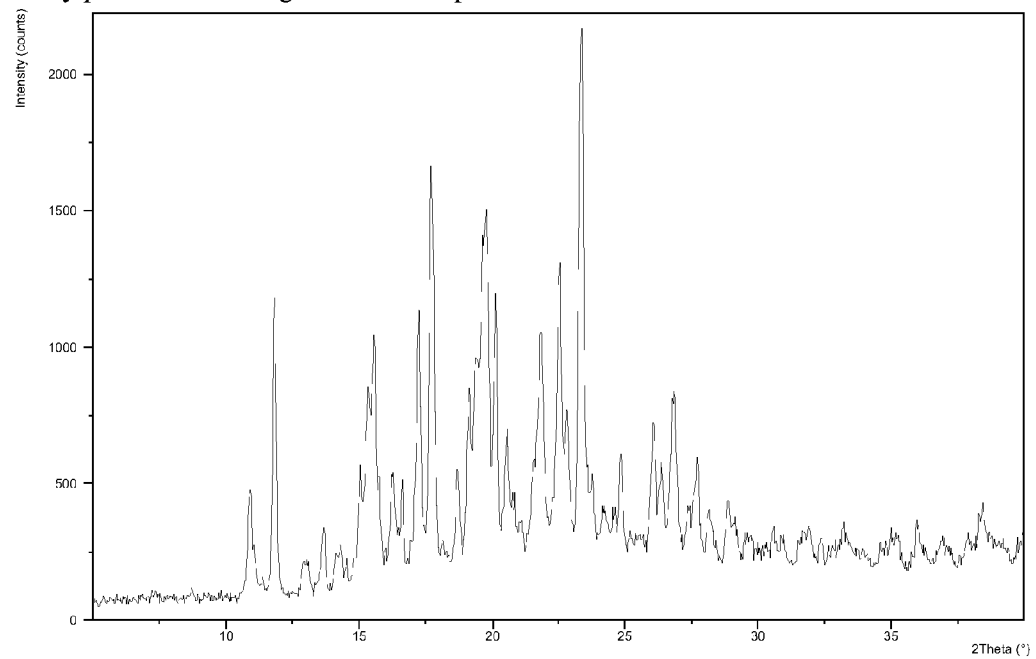

The sulphate, as prepared in example 11a, is crystalline (XRPD)—see FIG. 15. It has a melting point of ~166° C. The solubility in water is ~0.1 mg/ml.

Example 12a

Preparation of Phosphate of Compound I 11.1 ml of a 0.30 M solution of 1-[2-(2,4-Dimethylphenyl-sulfanyl)-phenyl]piperazine in acetone was treated with 0.2 ml 65% $H_3PO_4$ (aq). The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine phosphate was isolated in 1.23 gram (94%). NMR complies with structure. Elemental analysis: 54.21%; C, 7.15%; N, 6.43%; H. (Theory for a 1:1 salt: 54.53%; C, 7.07%; N, 6.36%; H).

Example 12b

Characterisation of the Phosphate of Compound I

Figure 16:
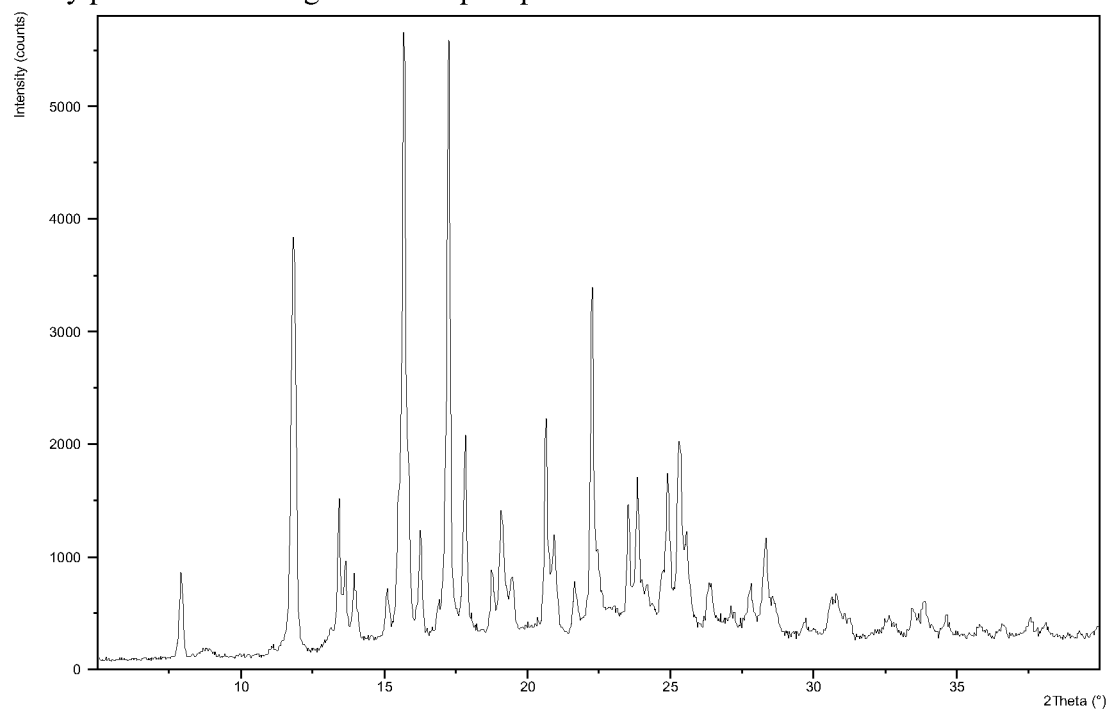

The phosphate, as prepared in example 12a, is crystalline (XRPD) see FIG. 16. It has a melting point of ~224° C. The solubility in water is ~1 mg/ml.

Example 13a

Preparation of Nitrate of Compound I 11.1 ml of a 0.30 M solution of 1-[2-(2,4-Dimethylphenyl-sulfanyl)-phenyl]piperazine in acetone was treated with 0.2 ml of 16.5 M $HNO_3$ (aq). The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine nitrate was isolated in 0.87 gram (73%).

NMR complies with structure. Elemental analysis: 59.80%; C, 11.67%; N, 6.51%; H. (Theory for a 1:1 salt: 59.81%; C, 11.63%; N, 6.41%; H).

Example 13b

Characterisation of the Nitrate of Compound I

Figure 17:
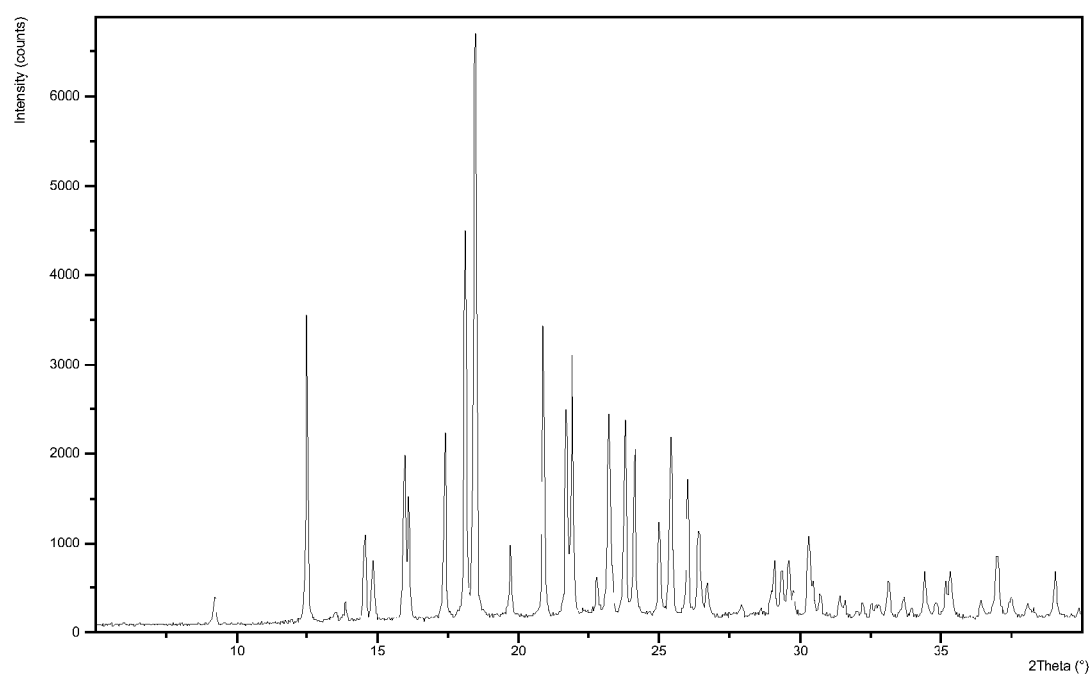
Figure 18A:
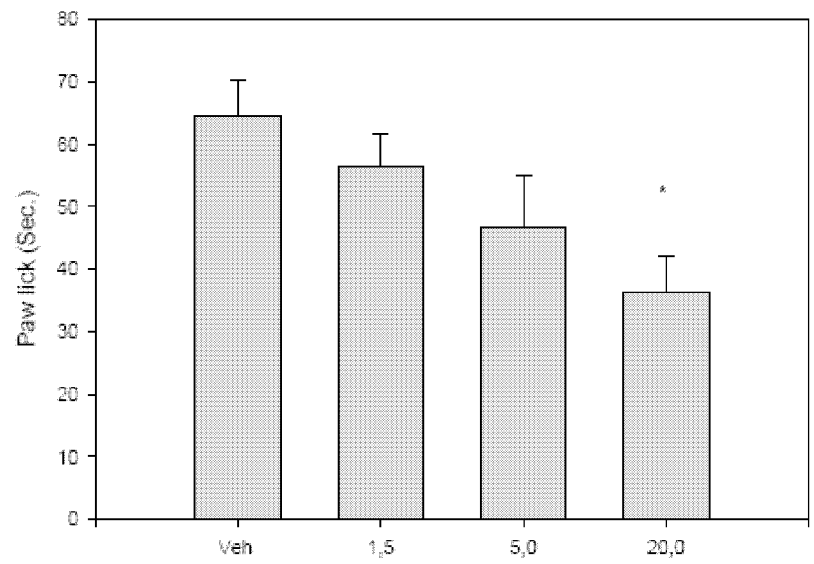
Figure 18B:
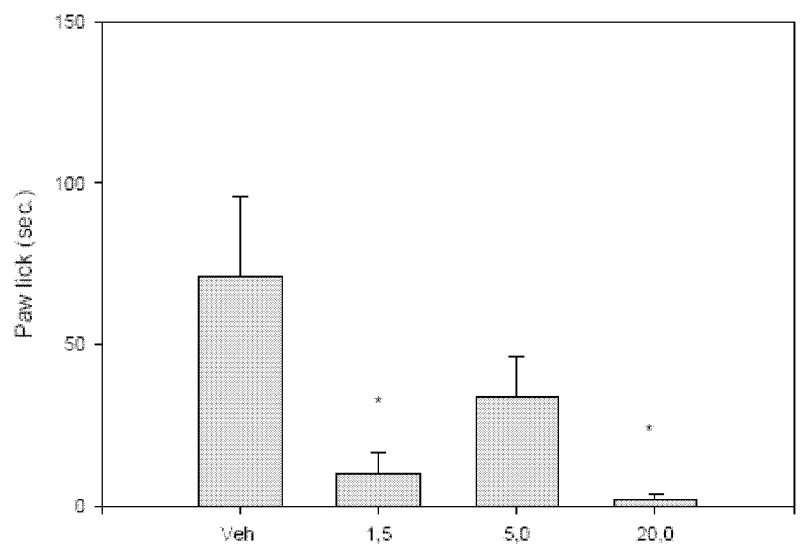

The nitrate, as prepared in example 13a, is crystalline (XRPD)—see FIG. 17. It does not melt but decomposes under an exothermic reaction at about 160° C. The solubility in water is ~0.8 mg/ml.

Example 14

Pain Effects in the Mouse Intradermal Formalin Test

In this model, mice receive an injection of formalin (4.5%, 20 µl) into the left hind paw. The irritation caused by the formalin injection elicits a characteristic biphasic behavioural response, as quantified by the amount of time spent licking the injured paw. The first phase (~0-10 minutes) represents direct chemical irritation and nociception, whereas the second (~20-30 minutes) is thought to represent pain of neuropathic origin. The two phases are separated by a quiescent period in which behaviour returns to normal. The effectiveness of test compounds to reduce the painful stimuli is assessed by counting the amount of time spent licking the injured paw in the two phases.

Compound I showed a significant reduction in second phase pain scores (FIG. 18b), indicating efficacy against pain of neuropathic origin. Furthermore, the compounds of the present invention showed a significant reduction in the first phase scores (FIG. 18a), indicating a more analgesic action at the highest dose. In summary, these results indicate that compounds of the present invention are likely to be effective in the treatment of pain disorders.

Example 15

Effects on Extracellular Levels of Acetylcholine in the Brain of Freely Moving Rats Methods
The animals were administered 1-[2-(2,4-dimethylphenyl-sulfanyl)phenyl]piperazine, HBr salt.
Animals
Male Sprague-Dawley rats, initially weighing 275-300 g, were used. The animals were housed under a 12-hr light/dark cycle under controlled conditions for regular in-door temperature (21±2° C.) and humidity (55±5%) with food and tap water available ad libitum.
Surgery and Microdialysis Experiments
Rats were anaesthetised with hypnorm/dormicum (2 ml/kg) and intracerebral guide cannulas (CMA/12) were stereotaxically implanted into the brain, aiming at positioning the dialysis probe tip in the ventral hippocampus (co-ordinates: 5.6 mm posterior to bregma, lateral −5.0 mm, 7.0 mm ventral to dura) or in the prefrontal cortex (co-ordinates: 3.2 mm anterior to bregma; lateral, 0.8 mm; 4.0 mm ventral to dura). Anchor screws and acrylic cement were used for fixation of the guide cannulas. The body temperature of the animals was monitored by rectal probe and maintained at 37° C. The rats were allowed to recover from surgery for 2 days, housed singly in cages. On the day of the experiment a microdialysis probe (CMA/12, 0.5 mm diameter, 3 mm length) was inserted through the guide cannula.

The probes were connected via a dual channel swivel to a microinjection pump. Perfusion of the microdialysis probe with filtered Ringer solution (145 mm NaCl, 3 mM KCl, 1 mM $MgCl_2$, 1.2 mM $CaCl_2$ containing 0.5 µM neostigmine) was begun shortly before insertion of the probe into the brain and continued for the duration of the experiment at a constant flow rate of 1 µl/min. After 180 min of stabilisation, the experiments were initiated. Dialysates were collected every 20 min. After the experiments the animals were sacrificed, their brains removed, frozen and sliced for probe placement verification.

The compound dissolved in 10% HPbetaCD and injected subcutaneously (2.5-10 mg/kg). Doses are expressed as mg salt/kg body weight. The compound was administered in a volume of 2.5 ml/kg.
Analysis of Dialysate Acetylcholine
Concentration of acetylcholine (ACh) in the dialysates was analysed by means of HPLC with electrochemical detection using a mobile phase consisting of 100 mM disodium hydrogenphosphate, 2.0 mM octane sulfonic acid, 0.5 mM tetramethyl-ammonium chloride and 0.005% MB (ESA), pH 8.0. A pre-column enzyme reactor (ESA) containing immobilised choline oxidase eliminated choline from the injected sample (10 µl) prior to separation of ACh on the analytical column (ESA ACH-250); flow rate 0.35 ml/min, temperature: 35° C. After the analytical column the sample passed through a post-column solid phase reactor (ESA) containing immobilised acetylcholineesterase and choline oxidase. The latter reactor converted ACh to choline and subsequently choline to betaine and $H_2O_2$. The latter was detected electrochemical by using a platinum electrode (Analytical cell: ESA, model 5040).

Data Presentation

In single injection experiments the mean value of 3 consecutive ACh samples immediately preceding compound administration served as the basal level for each experiment and data were converted to percentage of basal (mean basal pre-injection values normalized to 100%).

Results

The compound significantly increased extra-cellular levels of ACh in the rat prefrontal cortex and the ventral hippocampus—see FIGS. 19a and 19b.

Example 16

Contextual Fear Conditioning in Rats

The compound administered in the present experiment was 1-[2-(2,4-dimethylphenylsulfanyl)phenyl]piperazine HBr salt.

We have studied the effect of the compound on acquisition, consolidation and recall of contextual fear conditioning in rats. In the fear conditioning paradigm animals learn to associate a neutral environment (context, the training chamber, CS) with an aversive experience (an electrical foot-shock, US). During re-exposure to the training chamber, animals express a freezing behaviour, which is taken as a direct measure of the fear-related memory [Pavlov J. Biol. Sci., 15, 177-182, 1980]. The neuroanatomy of contextual fear conditioning has been thoroughly investigated and several studies have demonstrated that the hippocampus and amygdala are necessary for the formation of this memory [Hippocampus, 11, 8-17, 2001; J. Neurosci., 19, 1106-1114, 1999; Behav. Neurosci., 106, 274-285, 1992].

Animals and Drugs

Adult male Sprague-Dawley rats (weighing 250-300 g at time of training) from Charles River Laboratories, housed two per cage under a 12 h light/dark cycle, were used. Food and water were available ad libitum. Rats were used 1 week after arrival. The compound was dissolved in 10% HPbetaCD and injected subcutaneously. The drug was administered in a volume of 2.5 ml/kg.

Apparatus

Training and testing were conducted in a soundproof chamber (30×20×40 cm) housed in an isolated room and connected to a ventilation system. Illumination was provided by a white light (60 Watt). The floor of the chamber consisted of a metal grid attached to an electric shock generator. Prior to training and testing, the chamber was cleaned with a 70% ethanol solution. A video camera allowed for behavioral observations and recording of the training session for off-line analysis.

Acquisition and Retention Test

During the acquisition animals were allowed to freely explore the novel environment for a 1 min habituation period, which co-terminated with one inescapable foot-shock (unconditioned stimulus, US) through the electrifiable grid floor. The foot shock had a duration of 2 s and an intensity of 0.75 mA. Animals remained in the conditioning chamber for another 60 s after the US. Freezing behaviour was scored during the first 58 s (pre-shock acquisition; experimenter blinded to groups) to determine baseline-freezing responses to the context. At the end of the acquisition animals were gently removed and placed into their home cages. After 24 h the same animals were reintroduced into the training context (fear conditioning chamber) and a 2 min retention test was performed. During this period no foot shocks were applied. Freezing behaviour was scored during the whole test period with the experimenter blinded to groups and presented as percent of total test period.

Results and Discussion

Effect of the Compound on Contextual Fear Cognition in Rats

The effect of the compound on contextual fear conditioning in rats was studied (i) on acquisition (drug applied before acquisition, FIG. 20), (ii) on memory recall (drug applied before test, FIG. 21) and (iii) on consolidation (drug applied immediately after the acquisition, FIG. 22). In the first set of experiments, the compound (1, 5 and 10 mg/kg) was administered 1 h prior to the acquisition session. FIG. 20 depicts the acquisition of freezing behaviour during training (58 s prior to the food shock) and the retention test 24 after. The following findings were observed:

- The compound does not affect baseline freezing behaviour before the presentation of the foot shock at any dose tested.
- The compound at 5 mg/kg has a tendency to increase the time spent freezing during the retention test, 24 h after the acquisition (39.24±13.76%, n=6, versus 24.30±4.40%, n=16, in the vehicle-treated animals).
- The compound at 10 mg/kg significantly increases the time spent freezing during the retention test, 24 h after the acquisition (52.15±5.68%, n=10, versus 24.30±4.40%, n=16, in the vehicle-treated animals, p<0.01).

The fear conditioning model, as described in FIG. 20, is a standard procedure described in the literature for the investigation of learning and memory. In order to further elucidate the acute effects of this drug on memory recall, the compound (5, 10 and 20 mg/kg) was applied 1 h prior to the retention test. It was observed that the compound inhibits the expression of freezing behaviour at 5 mg/kg during the memory test (12.86±3.57%, n=9, versus 33.61±4.29%, n=13, in the vehicle-treated animals, p<0.05) (FIG. 21).

As described above, the compound by itself does not affect baseline freezing behaviour before the onset of US (FIG. 20), thus the most plausible hypothesis is that the observed effect in FIG. 21 is due to an anxiolytic effect. The conditioned memory is assessed via freezing behaviour, a response that is reduced by compounds with potential anxiolytic effects. This experiment demonstrates that the compound given acutely before memory recall has anxiolytic efficacy, it is therefore unlikely that increased freezing shown in FIG. 20 is due to an anxiogenic effect of the compound.

In order to strengthen that the compound is not anxiogenic but bears pro-cognitive potential, the compound was administered at 5, 10 and 20 mg/kg after the acquisition session. Consequently, in this set of experiments, the compound was onboard neither during the acquisition nor throughout the retention test. Here, it was observed that the compound at 5 mg/kg significantly enhances the time spent freezing during the retention test, 24 h after the acquisition session (45.58±4.50%, n=8, versus 25.26±3.57%, n=19, in the vehicle-treated animals, p<0.05). The percentage of time spent freezing during the context re-exposure has been described as a measure of a fear-related memory [*Pavlov J. Biol. Sci,* 15, 177-182, 1980], which is enhanced in compound-treated rats when compared to vehicle-treated animals (FIGS. 20 and 21). Taken together, the data show that the compound enhances contextual memory.

Example 17

Effect of Compound I in the Chronic Constriction Nerve Injury Model

Compound I was evaluated in the chronic constriction injury model [*Pain,* 33, 87-107, 1988]. This model of neuropathic pain involves the application of four loose ligations around one sciatic nerve of the rat over a period of time to develop both hyperalgesia and allodynia. The effect of test compounds in this test is measured as the time to withdraw the paw upon a thermal stimuli. Compound I (HBr salt) at 7.9 mg/kg s.c. 60 minutes) produced a significant and dose-dependant withdrawal latency following a thermal stimuli. These data (see FIG. 26) demonstrate that compound I has an analgesic-like effect.

The invention claimed is:

1. A method for the treatment of pain, the method comprising the administration of a therapeutically effective amount of 1-[2-(2,4-dimethylphenylsulfanyl)phenyl]piperazine or a pharmaceutically acceptable acid addition salt thereof (compound I) to a patient in need thereof.

2. The method according to claim 1, wherein compound I is the HBr acid addition salt.

3. The method according to claim 2, wherein said HBr acid addition salt is crystalline with XRPD reflections at 6.89, 9.73, 13.78 and 14.64 (° 2θ).

4. The method according to claim 3, wherein said HBr acid addition salts has an XRPD as depicted in FIG. 3.

5. The method according to claim 1, wherein compound I is administered in daily doses of about 1-20 mg.

* * * * *

UNITED STATES PATENT AND TRADEMARK OFFICE
CERTIFICATE OF CORRECTION

PATENT NO. : 8,664,225 B2
APPLICATION NO. : 12/527911
DATED : March 4, 2014
INVENTOR(S) : Nicholas Moore and Tine Bryan Stensbol It is certified that error appears in the above-identified patent and that said Letters Patent is hereby corrected as shown below:

In the Drawings

FIG. 1, line 1, delete "powdcr" and insert -- powder -- therefor.

FIG. 1, line 1, delete "frcc crystallinc basc:" and insert -- free crystalline base: -- therefor.

FIG. 6, line 1, delete "powdcr" and insert -- powder -- therefor.

FIG. 6, line 1, delete "mixturc" and insert -- mixture -- therefor.

FIG. 6, line 1, delete "cthylacctatc solvatc" and insert -- ethylacetate solvate -- therefor.

FIG. 19b, delete "  " and insert -- -- therefor.

In the Specification

Column 1, line 45, delete "On" and insert -- One -- therefor.

Column 1, line 62, delete "amitryline," and insert -- amitriptyline, -- therefor.

Column 1, line 63, delete "neuropatic" and insert -- neuropathic -- therefor.

Column 2, line 2, delete "neuropatic" and insert -- neuropathic -- therefor.

Column 2, line 6, delete "serotonine" and insert -- serotonin -- therefor.

Column 2, line 43, delete "phenyl-sulfanyl" and insert -- phenylsulfanyl -- therefor.

Column 2, line 66, delete "tatrate" and insert -- tartrate -- therefor.

Column 2, line 67, delete "tatrate" and insert -- tartrate -- therefor.

Column 3, line 1, delete "tatrate" and insert -- tartrate -- therefor.

Column 3, line 17, delete "phenyl]-piperazine" and insert -- phenyl]piperazine -- therefor.

Column 5, line 31, delete "casu" and insert -- case -- therefor.

Column 5, line 51, delete "(CPRS)," and insert -- (CRPS), -- therefor.

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,664,225 B2

Column 6, line 12, delete "bowl" and insert -- bowel -- therefor.

Column 6, line 63, delete "affect" and insert -- effect -- therefor.

Column 7, line 8, delete "know" and insert -- known -- therefor.

Column 7, lines 52-53, delete "phenyl]-piperazine" and insert -- phenyl]piperazine -- therefor.

Column 8, line 31, delete "phenyl-sulfanyl" and insert -- phenylsulfanyl -- therefor.

Column 8, line 40, delete "tabletting" and insert -- tableting -- therefor.

Column 10, line 43, delete "5HT3" and insert -- 5-HT$_3$ -- therefor.

Column 18, line 27, delete "piparazine," and insert -- piperazine, -- therefor.

Column 19, line 9, delete "acetylcholineesterase" and insert -- acetylcholinesterase -- therefor.